(12) United States Patent
Wilson et al.

(10) Patent No.: US 10,640,158 B2
(45) Date of Patent: May 5, 2020

(54) TRANSPORT CART FOR NUCLEAR MEDICINE/MOLECULAR IMAGING RADIOISOTOPES HAVING ENHANCED SAFETY FEATURES AND A PROCESS IMPLEMENTING THE SAME

(71) Applicant: Laurel Healthcare Solutions, Inc., Wexford, PA (US)

(72) Inventors: Lon Patrick Wilson, Wexford, PA (US); Ron Joseph Morosko, Jr., Wexford, PA (US)

(73) Assignee: Laurel Healthcare Solutions, Inc., Wexford, PA (US)

( * ) Notice: Subject to any disclaimer, the term of this patent is extended or adjusted under 35 U.S.C. 154(b) by 0 days.

(21) Appl. No.: 16/405,108

(22) Filed: May 7, 2019

(65) Prior Publication Data

US 2019/0254902 A1 Aug. 22, 2019

Related U.S. Application Data

(63) Continuation of application No. 15/357,257, filed on Nov. 21, 2016, now Pat. No. 10,278,877.
(Continued)

(51) Int. Cl.
*B62D 51/04* (2006.01)
*B62B 3/00* (2006.01)
(Continued)

(52) U.S. Cl.
CPC .............. *B62D 51/04* (2013.01); *A61B 6/037* (2013.01); *A61G 12/001* (2013.01); *B62B 3/003* (2013.01); *B62B 3/004* (2013.01); *B62B 3/04* (2013.01); *B62B 5/004* (2013.01); *B62B 5/0013* (2013.01); *B62B 5/04* (2013.01); *B62B 5/049* (2013.01); *A61G 2203/30* (2013.01); *A61G 2210/50* (2013.01); *B62B 5/0033* (2013.01); *B62B 5/0414* (2013.01); *B62B 5/0433* (2013.01); *B62B 2202/56* (2013.01);
(Continued)

(58) Field of Classification Search
CPC ...... A61G 12/001; B62B 3/002; B62B 3/004; B62B 3/005
See application file for complete search history.

(56) References Cited

U.S. PATENT DOCUMENTS

| | | | |
|---|---|---|---|
| 5,137,403 A | 8/1992 | McCaffrey |
| 5,845,914 A | 12/1998 | Lenkman |
| 5,873,585 A | 2/1999 | Engelking |
| 6,000,486 A | 12/1999 | Romick et al. |

(Continued)

*Primary Examiner* — Kevin Hurley
(74) *Attorney, Agent, or Firm* — BakerHostetler

(57) ABSTRACT

The disclosure relates to a medical imaging supply transport cart having enhanced safety features and a process implementing the same. The medical imaging supply transport cart includes a support surface configured to support medical imaging supplies, the support surface further configured to support a support mechanism, and the support mechanism further configured to support the medical imaging supplies. The support mechanism further configured to rigidly hold the medical imaging supplies with a first holding mechanism, the medical imaging supplies configured to store at least one dose of a nuclear medicine, a plurality of wheels arranged below the support surface, at least one door configured to enclose the medical imaging supplies, and a handle configured to be grasped by a user to guide the medical imaging supply transport cart.

21 Claims, 12 Drawing Sheets

Related U.S. Application Data

(60) Provisional application No. 62/257,956, filed on Nov. 20, 2015.

(51) Int. Cl.
    *B62B 5/00*     (2006.01)
    *B62B 5/04*     (2006.01)
    *A61B 6/03*     (2006.01)
    *A61G 12/00*    (2006.01)
    *B62B 3/04*     (2006.01)

(52) U.S. Cl.
    CPC ....... *B62B 2202/67* (2013.01); *B62B 2204/00* (2013.01); *B62B 2204/02* (2013.01); *B62B 2204/04* (2013.01)

(56) References Cited

U.S. PATENT DOCUMENTS

| | | |
|---|---|---|
| 6,820,878 B2 | 11/2004 | Safari et al. |
| 7,056,334 B2 | 6/2006 | Lennox |
| 7,665,811 B2 | 2/2010 | Johanning |
| 7,673,952 B2 | 3/2010 | Jeansonne et al. |
| 9,808,545 B2 | 11/2017 | Mauzerall et al. |
| 10,111,972 B2 * | 10/2018 | Mauzerall ............... A61L 2/26 |
| 2005/0057011 A1 | 3/2005 | Chang |
| 2006/0290083 A1 | 12/2006 | Ruiz |
| 2007/0228680 A1 | 10/2007 | Reppert et al. |
| 2008/0300572 A1 | 12/2008 | Rankers et al. |
| 2009/0315287 A1 | 12/2009 | Rossini |
| 2010/0145160 A1 | 6/2010 | Cinqualbre et al. |
| 2010/0185061 A1 | 7/2010 | Medve |
| 2015/0223890 A1 | 8/2015 | Miller et al. |
| 2015/0227127 A1 | 8/2015 | Miller et al. |
| 2018/0085480 A1 | 3/2018 | Mauzerall et al. |

\* cited by examiner

TRANSPORT CART FOR NUCLEAR
MEDICINE/MOLECULAR IMAGING
RADIOISOTOPES HAVING ENHANCED
SAFETY FEATURES AND A PROCESS
IMPLEMENTING THE SAME

CROSS REFERENCE TO PRIOR APPLICATIONS

This application is a continuation of the U.S. patent application Ser. No. 15/357,257, filed Nov. 21, 2016 now U.S. Pat. No. 10,278,877 issued May 7, 2019, which is incorporated herein by reference in its entirety, which claims the benefit from U.S. Provisional Application No. 62/257,956 filed on Nov. 20, 2015, which is hereby incorporated by reference for all purposes as if fully set forth herein.

BACKGROUND OF THE DISCLOSURE

1. Field of the Disclosure

The disclosure relates to a nuclear medicine/molecular imaging radioisotope transport cart having enhanced safety features and a process implementing the same.

2. Related Art

A number of nuclear medicine/molecular imaging radioisotope dose supply devices exist for supplying doses of nuclear medicine/molecular imaging radioisotopes and generator isotopes via unit dose, generators, and/or infusion systems to aid physicians in delivering these doses of radioisotopes to patients for performing diagnostic imaging procedures. However, these supply devices are costly and complex. Accordingly, physicians will often times have the supply devices delivered to medical facilities for a limited time to perform the diagnostic procedures. The Food and Drug Administration (FDA) requires that some of these supply devices be delivered consistent with a stringent set of rules. This stringent set of rules increases complexity and costs associated with using the supply devices, such as, the radioisotope for cardiac PET imaging, Rb-82. What is not allowed is the moving of the Rb-82 "generator" due to sterility issues with connection and disconnection of the Rb-82 isotope product from the infusion system. What is allowed is a Rb-82 generator together with the infusion system to be placed into a tractor trailer unit and transported as long as the Rb-82 product does not get disengaged from the infusion system and is contained in a self-contained transportable trailer that is climate controlled (24/7). This increases complexity and costs associated with using the supply devices.

Additionally, molecular isotopes, such as Fluorine 18, are packaged in lead encased containers which have a minimum of 1 inch lead shielding and weigh between 21 to 40 pounds each. The transport of this and similar products is also subject to increased complexity and cost.

Accordingly, a transport cart for nuclear medicine/molecular imaging radioisotopes having enhanced safety features and a process implementing the same is needed to reduce the complexity and costs and increase security associated with using nuclear medicine/molecular imaging radiopharmaceutical dose and supply devices.

SUMMARY

The foregoing needs are met, to a great extent, by the disclosure, wherein in one aspect a technique and apparatus are provided to provide a radioisotope nuclear medicine/molecular imaging transport cart.

The nuclear medicine/molecular imaging radioisotopes may include, but are not limited to unit dose radiopharmaceuticals, bulk radioisotopes, generator systems, infusion systems for generator radioisotope systems, and the like hereinafter referred to as "medical imaging supplies." The radioisotope nuclear medicine/molecular imaging transport cart is configured to transport the medical imaging supplies and is hereafter referred to as "medical imaging supply transport cart."

In one aspect, a medical imaging supply transport cart includes a support surface configured to support medical imaging supplies, the support surface further configured to support a support mechanism, the support mechanism further configured to support the medical imaging supplies, the support mechanism further configured to rigidly hold the medical imaging supplies with a first holding mechanism, a plurality of wheels arranged below the support surface, at least one door configured to enclose the medical imaging supplies, and a handle configured to be grasped by a user to guide the medical imaging supply transport cart.

In one aspect, a medical imaging supply transport cart includes a support surface configured to support medical imaging supplies, the support surface further configured to support a support mechanism, the support mechanism further configured to support the medical imaging supplies, the support mechanism further configured to rigidly hold the medical imaging supplies with a first holding mechanism, the medical imaging supplies configured to store at least one dose of a nuclear medicine, a plurality of wheels arranged below the support surface, at least one door configured to enclose the medical imaging supplies, a handle configured to be grasped by a user to guide the medical imaging supply transport cart, a second holding mechanism configured to rigidly secure the medical imaging supply transport cart within a small delivery truck during transportation, and at least one locking mechanism associated with the at least one door, the at least one locking mechanism configured to lock the at least one door in a closed position, wherein the support mechanism comprises a self-leveling mechanism, wherein the support mechanism comprises a shock absorbing mechanism, wherein the plurality of wheels comprise a plurality of casters, wherein the plurality of wheels are configured with brake mechanisms, and wherein the plurality of wheels are each configured with a shock absorber.

In one aspect, a medical imaging supply transport cart includes a support surface configured to support medical imaging supplies, the support surface further configured to support a support mechanism, the support mechanism further configured to support the medical imaging supplies, the support mechanism further configured to rigidly hold the medical imaging supplies with a first holding mechanism, the medical imaging supplies configured to store at least one dose of a nuclear medicine, a plurality of wheels arranged below the support surface, at least one door configured to enclose the medical imaging supplies, a handle configured to be grasped by a user to guide the medical imaging supply transport cart, a second holding mechanism configured to rigidly secure the medical imaging supply transport cart within a small delivery truck during transportation, at least one of the following: environmental systems, sensor systems, a redundant power backup system, and nuclear medicine monitoring systems, and at least one monitoring device configured to monitor at least one of the following: the environmental systems, the sensor systems, the redundant power backup system, and the nuclear medicine monitoring systems, and at least one locking mechanism associated with the at least one door, the at least one locking mechanism configured to lock the at least one door in a closed position, wherein the support mechanism comprises a self-leveling mechanism, wherein the support mechanism comprises a shock absorbing mechanism, wherein the plurality of wheels comprise a plurality of casters, wherein the plurality of wheels are configured with brake mechanisms, and wherein the plurality of wheels are each configured with a shock absorber.

There has thus been outlined, rather broadly, certain aspects of the disclosure in order that the detailed description thereof herein may be better understood, and in order that the present contribution to the art may be better appreciated. There are, of course, additional aspects that will be described below and which will form the subject matter of the claims appended hereto.

In this respect, before explaining at least one aspect in detail, it is to be understood that aspects of the disclosure are not limited in its application to the details of construction and to the arrangements of the components set forth in the following description or illustrated in the drawings. Aspects of the disclosure are capable of aspects in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of aspects of the disclosure. It is important, therefore, that the claims be regarded as including such equivalent constructions insofar as they do not depart from the spirit and scope of aspects of the disclosure.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION

Figure 1:
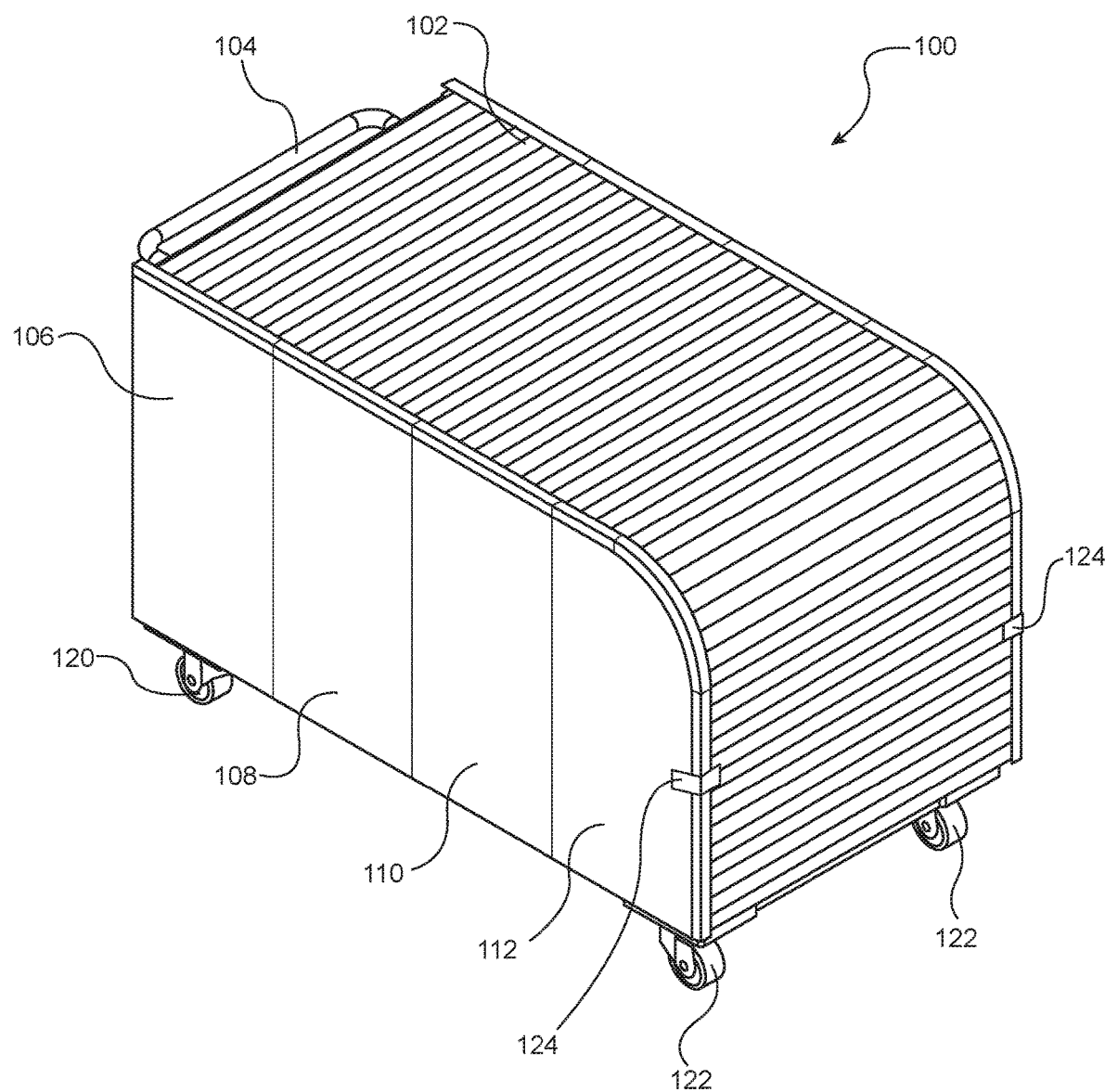
FIG. 1 shows a perspective view of a medical imaging supply transport cart with doors and top in a closed configuration constructed according to the principles of the disclosure.

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

The disclosure relates to a medical imaging supply transport cart having enhanced safety features and a process implementing the same. The medical imaging supply transport cart may operate as a relocatable box, a simple mode of transportation for self-contained medical radioisotopes for the nuclear medicine industry, including infusion cart systems, radioisotopes, radiopharmaceuticals or the like and their unit dose delivery systems. The medical imaging supply transport cart allows for more secure transport of unit dose or generator radioisotopes from one location to another in the form of an enclosed cart with locking mechanisms for security. The medical imaging supply transport cart may be a wheeled cart making transportation of the aforementioned products less burdensome. In one aspect the cart may be propelled by human-force. In one aspect the cart may be self-propelled.

The medical imaging supply transport cart may provide an enclosed space for the aforementioned products to be placed, completely intact, so that they can be wheeled from place to place with ease. The wheels may provide not only the ability for the medical imaging supply transport cart to be mobile, but may provide shock absorption so products enclosed in the medical imaging supply transport cart will be minimally impacted during transit.

Products may be placed inside of a body of the medical imaging supply transport cart through a door of the medical imaging supply transport cart body. Once placed inside, the materials may be secured in place by tension tie downs to ensure secure placement. The product may not be intended to be deconstructed in any manner for placement inside the medical imaging supply transport cart. Once inside, the door may be closed and latched to create a full enclosure around product. The medical imaging supply transport cart can then be pushed from place to place as needed.

The medical imaging supply transport cart may be equipped with wheel brakes allowing the medical imaging supply transport cart to remain steady when it is stopped and products are being loaded and unloaded. In addition, the medical imaging supply transport cart may be equipped with a shock absorbing mechanism in the form of shock absorbers on each wheel to ensure stable transport to and from use locations. Locations of transport may include but are not limited to: medical department to medical department, delivery vehicle to medical procedure room, medical laboratory to patient bedside, laboratory to imaging suite, and the like.

The medical imaging supply transport cart may maintain constant power (redundant power backup system), may include environmental systems, may be configured to fit through a 36" wide by 6' high door, and may have an air ride suspension/anti-vibration flooring.

The medical imaging supply transport cart may be implemented to have constant power (always on), temperature controlled HVAC (24/7/365), humidity sensors/warning system, heat/cold sensor warning system, battery backup—redundant system, air ride suspension, leveling system, vibration sensors, on board Global Navigation Satellite System (GNSS) locater, 24/7 connectivity to operations base for sensor detection systems, door open sensor/warning, available with electric motor drive, security locks, all supplies, meets all mobile Positron Emission Tomography (PET) suite requirements, and meets all United States Nuclear Regulatory Commission (USNRC) licensed material requirements.

The medical imaging supply transport cart may be associated with a Power Pusher™, certified for Class 1, Division 1, Group D areas, and may be designed to tackle challenging applications in demanding environments. With a temperature classification rating of T4, it can withstand temperatures reaching 135° C. The device pushes or pulls carts, dollies, vats and more, weighing up to 25,000 pounds. Plus, with a wide variety of application-specific attachments available, it can be customized for a high-quality, heavy-duty tug for challenging environments.

FIG. 1 shows a perspective view of a medical imaging supply transport cart with doors and top in a closed configuration constructed according to the principles of the disclosure. In particular, FIG. 1 shows the medical imaging supply transport cart 100 having a top door 102 and one or more side doors 106, 108, 110, 112. The side opposite the one or more side doors 106, 108, 110, 112 may further include additional side doors arranged in a consistent symmetrical manner. Alternatively, the side opposite the one or more side doors 106, 108, 110, 112 may not include any doors.

In one aspect shown in FIG. 1, the top door 102 may have a multi-slat tambour door construction. In this aspect, the top door 102 may roll up when opened. For example roll on to a roller for storage within a housing 302 or the like. In other aspects, the top door 102 may be a single piece or multipiece hinged structure (see FIG. 10). In other aspects, the top door 102 may be a folding structure, a cloth structure, an air bubble plexiglass construction, may be a canvas structure, a blowup structure, and the like. The top door 102 may include any type of metallic or synthetic material.

The medical imaging supply transport cart 100 may include back wheels 120 and front wheels 122. The medical imaging supply transport cart 100 may further include a push handle 104 for a user to manually move the medical imaging supply transport cart 100. The medical imaging supply transport cart 100 may further include one or more locking mechanisms 124 to lock the one or more side doors 106, 108, 110, 112 in a closed manner. In one aspect, the locking mechanism 124 may further lock the one or more side doors 106, 108, 110, 112 to the top door 102 in order to keep both securely locked and closed. In one aspect the lock may be implemented as a warded lock, pin tumbler lock, a wafer tumbler lock, a disc tumbler lock, a lever tumbler lock, a padlock, and the like. In one aspect the lock may be implemented as an electronic lock. The electronic lock may include a keycard lock, smart lock, a sidebar lock, magnetic locks, and the like. In one aspect, the locking mechanism 124 may simply keep the one or more side doors 106, 108, 110, 112 and the top door 102 securely closed.

In certain aspects, the medical imaging supply transport cart 100 may be configured such that it has environmental/weather protections. For example, the top door 102 and the one or more side doors 106, 108, 110, 112 may include environmental or whether protective features operating as a barrier for rain, snow, extreme temperatures, and the like. Moreover, the top door 102 and the one or more side doors 106, 108, 110, 112 may include insulation and/or a thermal shield for maintaining temperature.

In further aspects, the surface of the medical imaging supply transport cart 100 may include anti-microbial surface materials that are easily cleaned and disinfected. For example, paints that are anti-microbial, an antimicrobial agent that inhibits or reduces the ability of microorganisms to grow on the surface of a material, and the like.

Figure 2:
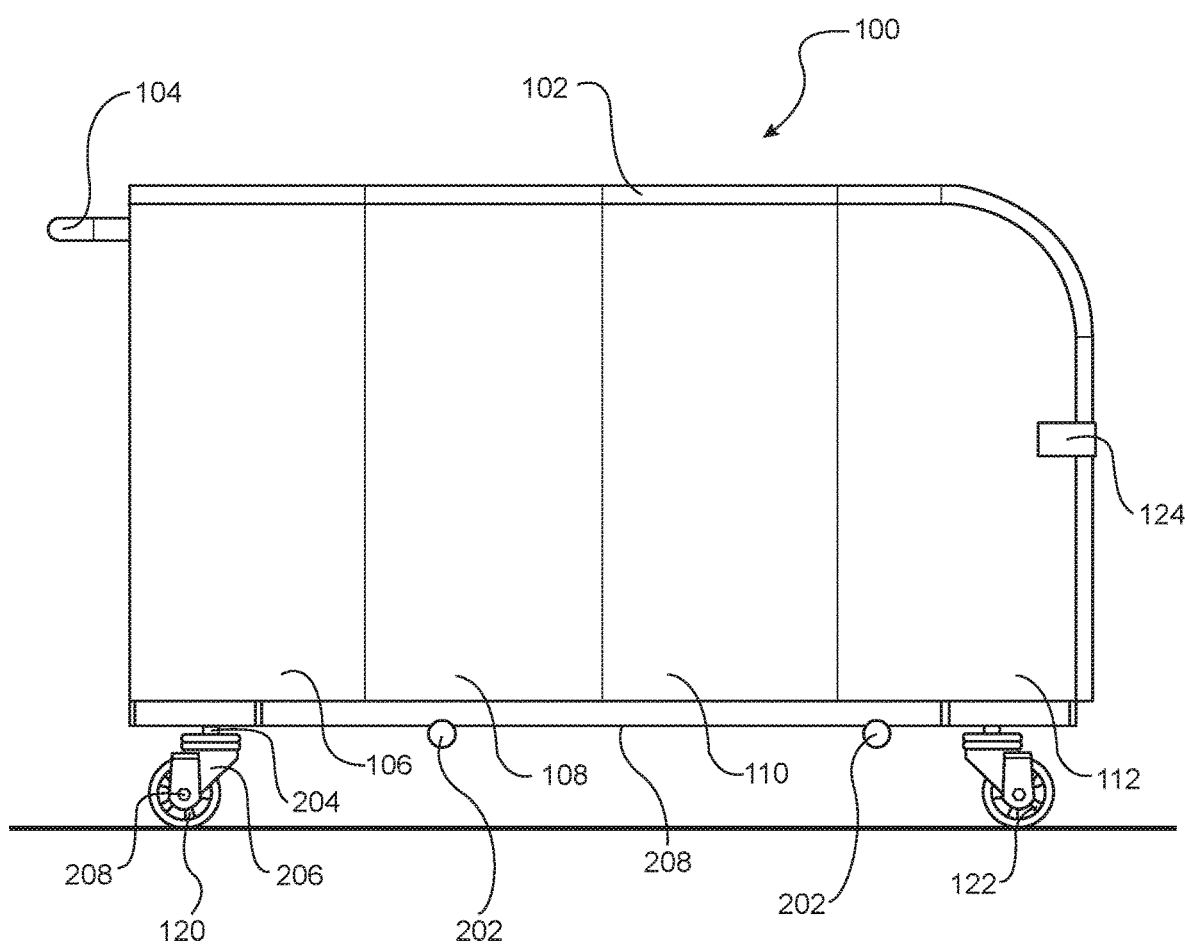
FIG. 2 shows a side view of the medical imaging supply transport cart of FIG. 1.

FIG. 2 shows a side view of the medical imaging supply transport cart of FIG. 1. The medical imaging supply transport cart 100 may include tie down rings 202. The tie down rings 202 may be configured to tie down the medical imaging supply transport cart 100 with tie down straps during transport in a small delivery truck, or the like. The tie down rings 202 may be metallic rings pivotably attached to a bottom portion 208 of the medical imaging supply transport cart 100. Other locations for the tie down rings 202 are contemplated as well. The tie down straps may be implemented as ratchet straps, lashing straps, tie downs or the like and may include fasteners used to hold down the medical imaging supply transport cart 100 during transport. The tie down straps may include webbing that is outfitted with tie down hardware.

In some aspects, the medical imaging supply transport cart 100 may include an engagement mechanism configured to engage with a lift system associated with the small delivery truck. In this aspect, the engagement mechanism may ensure a firm mechanical connection with the lift system to allow the small delivery truck to lift the medical imaging supply transport cart 100 into the truck or lower the medical imaging supply transport cart 100 out of the truck. The engagement mechanism may be implemented as hooks, rings, open ended box structures and the like to connect to the lift system. The lift system in the small delivery truck may be a hydraulic lift system, an electromechanical lift system, a mechanical lift system, a pneumatic lift system, and the like.

FIG. 2 further shows details of the back wheels 120. The back wheels 120 may be implemented as swivel casters. A swivel caster implementation may allow for movement in multiple directions, may have one or two sets of raceways that allow the caster to swivel 360 degrees under a load. A swivel caster implementation may include locking casters, kingpin-less casters, hollow kingpin casters, plate casters, stem casters, and the like. In other aspects, the back wheels 120 may be implemented as rigid casters. The rigid caster implementation may only allow forward and backward movement.

The back wheels 120 may include a yoke 206. The yoke 206 may be implemented as part of a swivel or rigid caster and can be considered a frame. The yoke 206 may serve to hold the back wheel 120 in place. The yoke 206, working with a swivel head allows the back wheel 120 to operate in a 360 degree manner. The back wheels 120 may also be lockable in some aspects. The back wheels 120 may include a spring mechanism 204. The spring mechanism 204 may include a shock absorbing or vibration dampening mechanism and may be implemented with a spring mechanism. The spring mechanism may be a coiled steel spring, or the like. The shock absorbing or vibration dampening function may also be implemented with a hydraulic mechanism, elastomeric springs, and/or shock absorbers (described in greater detail below). The back wheels 120 may be constructed with materials that include elastomers (rubber and polyurethane), phenolic, nylons, pneumatic tires, steel, and the like dependent on application factors such as floor conditions, load, rollability, speed and climate. The back wheels 120 may be sized (diameter) dependent on application factors such as floor conditions, load, rollability, speed and climate. In one aspect, the back wheels 120 may further include non-marring materials. In one aspect, the back wheels 120 may further include anti-microbial materials. The back wheels 120 may include a brake mechanism. The brake mechanism may include a foot operated lever that includes a frictional element that engages a portion of the back wheels 120 and increases rotational friction to the back wheels 120. Hence, the brake mechanism prevents or limits rotation of the back wheels 120 when engaged. In other aspects, the brakes may be dead man type brakes requiring the user to actuate a lever to release the brakes. In other aspects, the brakes may be electric brakes that include a solenoid and the like for a braking functionality. Other types of brake mechanisms are contemplated as well. The front wheels 122 may be implemented with a number of the same features as described above in relation to the back wheels 120. In one aspect, the front wheels 122 may be implemented in a manner similar to the back wheels 120. In another aspect, the front wheels 122 may be implemented in a different manner than the back wheels 120.

Figure 3:
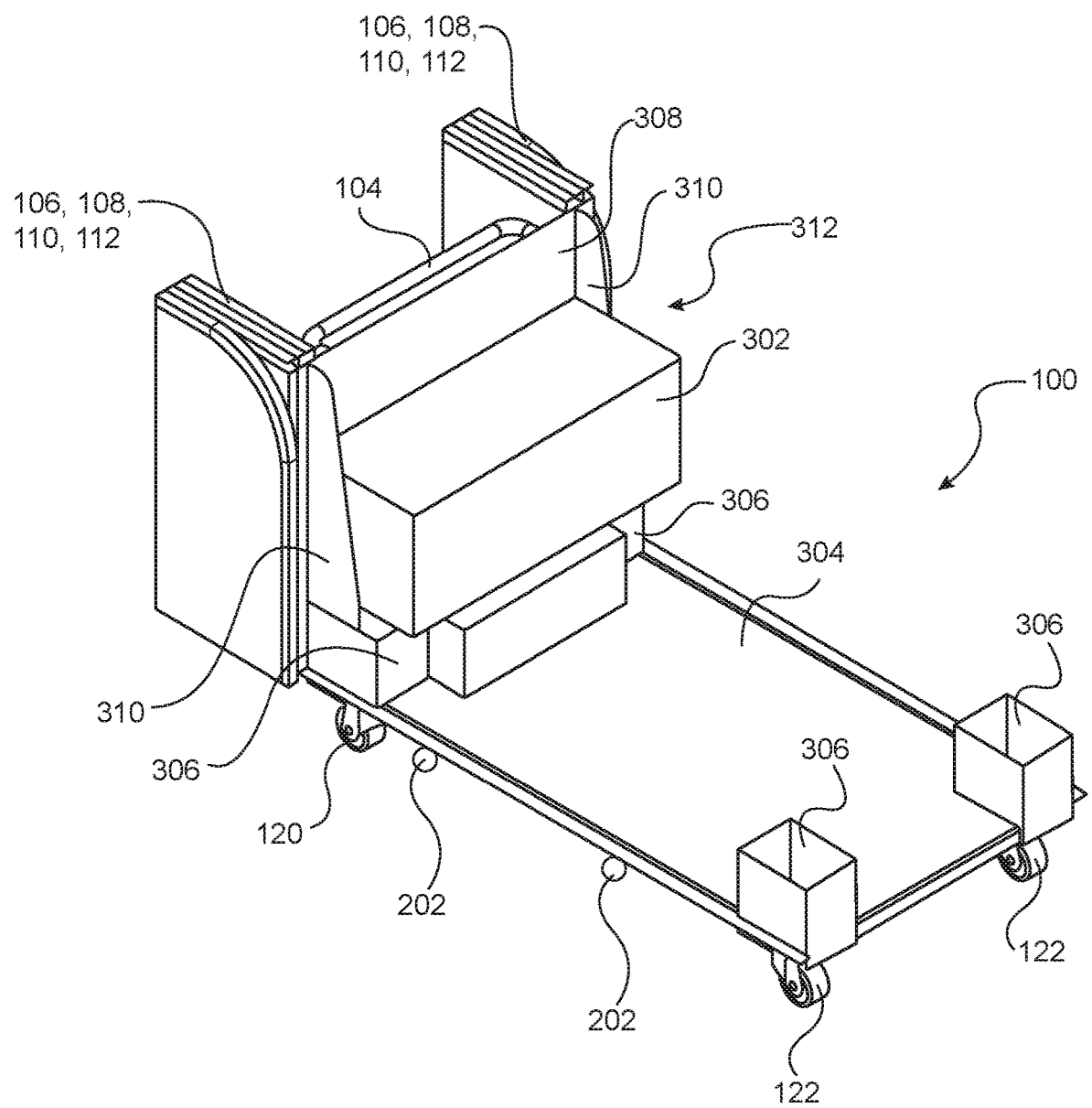
FIG. 3 shows a perspective view of the medical imaging supply transport cart of FIG. 1 with doors and top in an open configuration.

FIG. 3 shows a perspective view of the medical imaging supply transport cart of FIG. 1 with doors and top in an open configuration. In particular, FIG. 3 shows the medical imaging supply transport cart 100 with the one or more side doors 106, 108, 110, 112 in the open position and the top door 102 in the open position as well. The medical imaging supply transport cart 100 may include a floor 304 configured to support the medical imaging supplies 402 illustrated in FIG. 4 and described in greater detail below. The medical imaging supply transport cart 100 may include a rear wall 308 and sidewalls 310.

In certain aspects, the floor 304 may be configured to move vertically. In one such aspect, the floor 304 may be configured to lower to a floor surface through an actuation mechanism and thereafter configured to raise to the vertical position shown in FIG. 3. Such aspects allow the various components of the medical imaging supplies 402 to be easily removed from the medical imaging supply transport cart 100. For example, if the medical imaging supplies 402 are supported by wheels (see FIG. 12), then the medical imaging supplies 402 may be easily rolled off the medical imaging supply transport cart 100. The actuation mechanism may include a hydraulic system, pneumatic system, mechanical system, or the like that supports the floor 304 in both the raised position shown in FIG. 3 and a position where the floor 304 is adjacent the floor surface supporting the wheels 120. In other aspects, the floor 304 may be pivotally supported at one end adjacent to the wall 308 and the floor 304 may pivot such that a front edge adjacent the front wheels 122 is at floor height. Again this movement may be implemented by the actuation mechanism. In aspects where the actuation mechanism implemented as the hydraulic system, the hydraulic system may include a source of pressurized hydraulic fluid, a hydraulic cylinder to move the floor 304, and a controller that controls both the pressurized hydraulic fluid source and the hydraulic cylinder. In aspects where the actuation mechanism implemented as the pneumatic system, the pneumatic system may include a source of pressurized pneumatic fluid, a pneumatic cylinder to move the floor 304, and a controller that controls both the pressurized pneumatic fluid source and the pneumatic cylinder. In aspects where the actuation mechanism implemented as the mechanical system, the mechanical system may include a source of mechanical movement such as an electric motor or a hand-crank, a mechanical device such as a rack and pinion, gears, chains, and the like to move the floor 304, and a controller that controls both.

The medical imaging supply transport cart 100, including the rear wall 308, the sidewalls 310, the floor 304, the one or more side doors 106, 108, 110, 112 may be constructed of metallic materials, synthetic materials, or the like. The metallic materials may include steel, aluminum, stainless steel, and the like. The synthetic materials may include thermoplastic polymer materials such as polyacetal, polyacrylic, styrene acrylonitrile, acrylonitrile-butadiene-styrene (ABS), polycarbonate, polystyrene, polyethylene, polyphenylene ether, polypropylene, polyethylene terephthalate, polybutylene terephthalate, Nylons (Nylon-6, Nylon-6/6, Nylon-6/10, Nylon-6/12, Nylon-11 or Nylon-12, for example), polyamideimide, polyarylate, polyurethane, ethylene propylene diene rubber (EPR), ethylene propylene diene monomer (EPDM), polyarylsulfone, polyethersulfone, polyphenylene sulfide, polyvinyl chloride, polysulfone, polyetherimide, polytetrafluoroethylene, fluorinated ethylene propylene, perfluoroalkoxyethylene, polychlorotrifluoroethylene, polyvinylidene fluoride, polyvinyl fluoride, polyetherketone, polyether ether ketone (PEEK), and the like.

The medical imaging supply transport cart 100 may include portions 306 that provide reinforcement to support the back wheels 120 and front wheels 122. The portions 306 may further include the shock absorbing or vibration dampening mechanism. As further shown in FIG. 3, the medical imaging supply transport cart 100 may further include a housing 302 for housing a monitoring system 312, an environmental control system, a power supply system, medical supplies, and the like as described in greater detail below. In a further aspect, the housing 302 may include a lead lined medical waste container. The lead lined medical waste container may be for receiving IV line, gloves, syringes and the like medical waste that has been exposed to radiological material. In one aspect, the lead lined medical waste container may include a sharps container.

Figure 4:
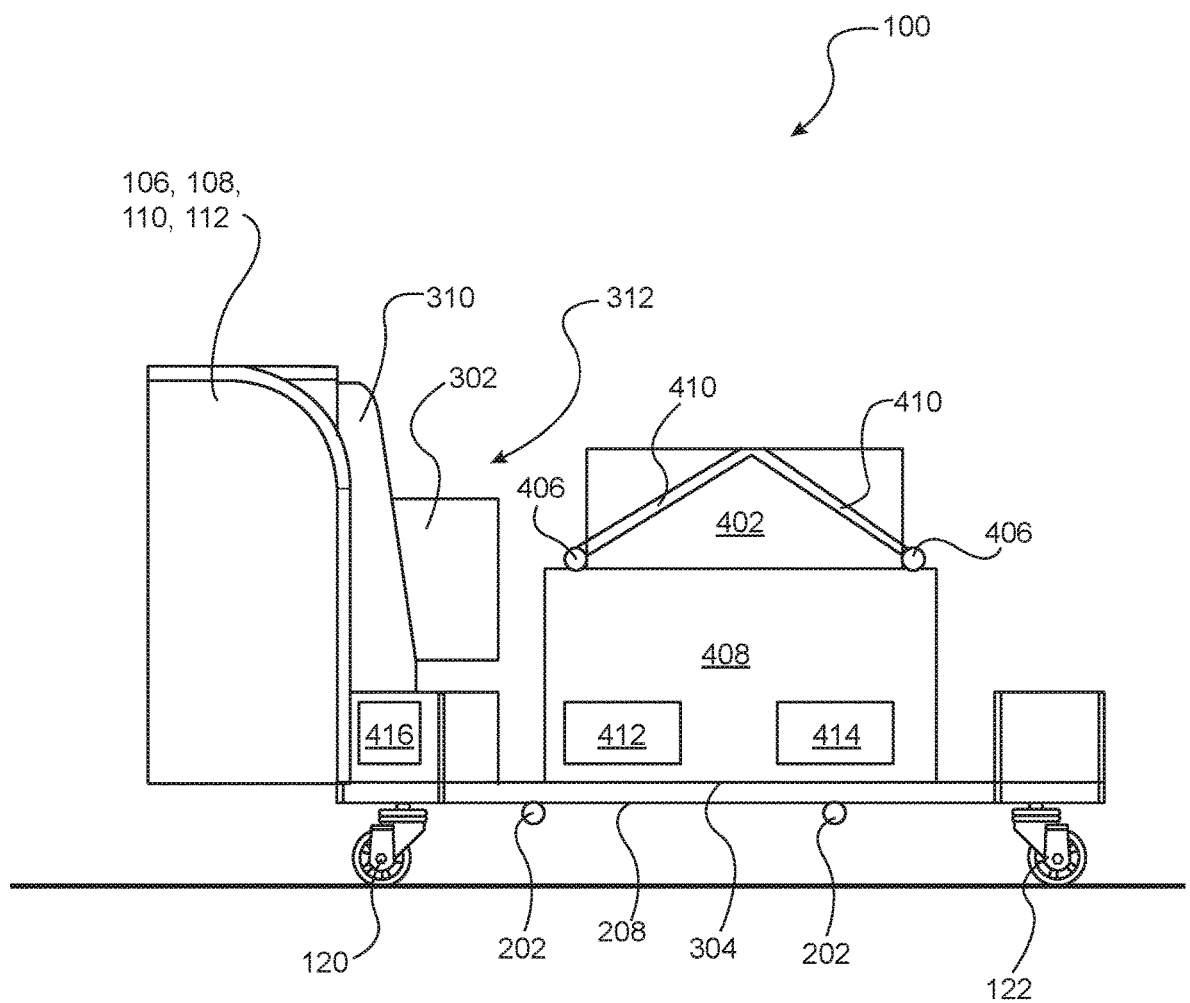
FIG. 4 shows a side view of the medical imaging supply transport cart of FIG. 1 with doors and top in an open configuration and with a medical imaging supplies mounted therein.

FIG. 4 shows a side view of the medical imaging supply transport cart of FIG. 1 with doors and top in an open configuration and with a medical imaging supplies mounted therein. In particular, FIG. 4 shows medical imaging supplies 402. In one aspect, a portion of the medical imaging supplies 402 may be regularly used for clinical purposes while remaining in and/or on the medical imaging supply transport cart 100. In another aspect, a portion of the medical imaging supplies 402 may be regularly used for clinical purposes after being removed from the medical imaging supply transport cart 100. The medical imaging supplies 402 may include an identification device consistent with one or more of the features a medical imaging supply transport cart monitoring device 604 described in detail below.

In one aspect, the medical imaging supplies 402 may be utilized in conjunction with Positron Emission Tomography (PET) imaging systems. The PET imaging system is a nuclear medicine, functional imaging system implementing a technique that is used to observe metabolic processes in the body. The PET imaging system detects pairs of gamma rays emitted indirectly by a positron-emitting radionuclide (tracer), which is introduced into the body on a biologically active molecule. Three-dimensional images of tracer concentration within the body are then constructed by computer analysis. In modern PET-CT scanners, three dimensional imaging is often accomplished with the aid of a CT X-ray scan performed on the patient during the same session, in the same machine.

The medical imaging supplies 402 may be configured to store and provide dose quantities of radionuclides to the patient for use with the PET imaging system. Radionuclides used in PET scanning are typically isotopes with short half-lives such as carbon-11, nitrogen-13, oxygen-15, fluorine-18, gallium-68, zirconium-89, rubidium-82, or the like. These radionuclides are incorporated either into compounds normally used by the body such as glucose (or glucose analogues), water, or ammonia, or into molecules that bind to receptors or other sites of drug action. In one aspect, the radionuclides transported by the medical imaging supplies include rubidium-82. It is contemplated that the medical imaging supplies 402 may be used for many other types of nuclear medicine systems including but not limited to unit dose radiopharmaceuticals, bulk radioisotopes, generator systems, infusion systems for generator radioisotope systems, Technetium-99 m, and the like.

Additionally, the medical imaging supplies 402 may include molecular isotopes, such as Fluorine 18, that may be packaged in lead encased containers which have a minimum of 1 inch lead shielding and weigh between 21 to 40 pounds each. By placing these lead containers into the medical imaging supply transport cart 100, secure and reduced handling can be achieved, the radiation exposure to medical personnel is reduced, as well as the human factor of carrying heavy lead radioisotope containers by hand can be avoided to increase safety. An enhanced feature of a specialized radiopharmaceutical medical imaging supply transport cart 100 is the asset management of the radiopharmaceutical as well as the authentication of licensed personnel granted access to use high energy radioisotopes.

The medical imaging supplies 402 may be supported on a support 408. The support 408 may include tie down rings 406. The tie down rings 406 may be configured to tie down the medical imaging supplies 402 with tie down straps 410 during transport in a small delivery truck, or the like. The tie down rings 406 may be metallic rings pivotably attached to a top portion the support 408 of the medical imaging supply transport cart 100. Other locations for the tie down rings 406 are contemplated as well. The tie down straps 410 may be implemented as ratchet straps, lashing straps, tie downs or the like and may include fasteners used to hold down the medical imaging supplies 402 during transport. The tie down straps 410 may include webbing that is outfitted with tie down hardware. In other aspects, in addition to or instead of tiedown straps 410, the medical imaging supplies 402 may be secured with netting, ratchet straps, cable structures, or like load securing mechanisms.

The support 408 may include a self-leveling mechanism 412 and/or a shock absorbing mechanism 414. The self-leveling mechanism 412 may include hydropneumatic system, self-energizing hydraulic strut, air suspension, and the like. In one aspect, the shock absorbing mechanism 414 may implemented with twin-tube shock absorbers, twin-tube gas charged shock absorbers, position sensitive damping shock absorbers, acceleration sensitive damping shock absorbers, coilover shock absorbers, and the like.

In one aspect, one or more of the back wheels 120 and the front wheels 122 may be driven such that the medical imaging supply transport cart 100 is self-propelled. In this regard, one or more of the back wheels 120 and the front wheels 122 may include a pusher mechanism 416. The pusher mechanism 416 may include a motor, a transmission, a controller, a power source, user controls, and the like. The motor may be an electric motor that receives power from the power source such as a battery and is controlled by the controller in response to operation of the user controls. The user controls may be mounted on the push handle 104. The motor may rotate the transmission and the transmission may deliver the rotation to the one or more of the back wheels 120 and/or the front wheels 122. The pusher mechanism 416 may be certified for Class 1, Division 1, Group D areas, may be implemented to tackle challenging applications in demanding environments. The pusher mechanism 416 may be implemented with a temperature classification rating of T4 and can withstand temperatures reaching 135° C. Alternatively, the pusher mechanism 416 may be implemented as a separate device and the medical imaging supply transport cart 100 may be configured to receive a portion of the pusher mechanism 416 for movement of the medical imaging supply transport cart 100. In some aspects, the pusher mechanism 416 is integrated into the medical imaging supply transport cart 100. In other aspects, the pusher mechanism 416 is separate from the medical imaging supply transport cart 100 and the medical imaging supply transport cart 100 includes an engagement mechanism to engage with the pusher mechanism 416.

Figure 5:
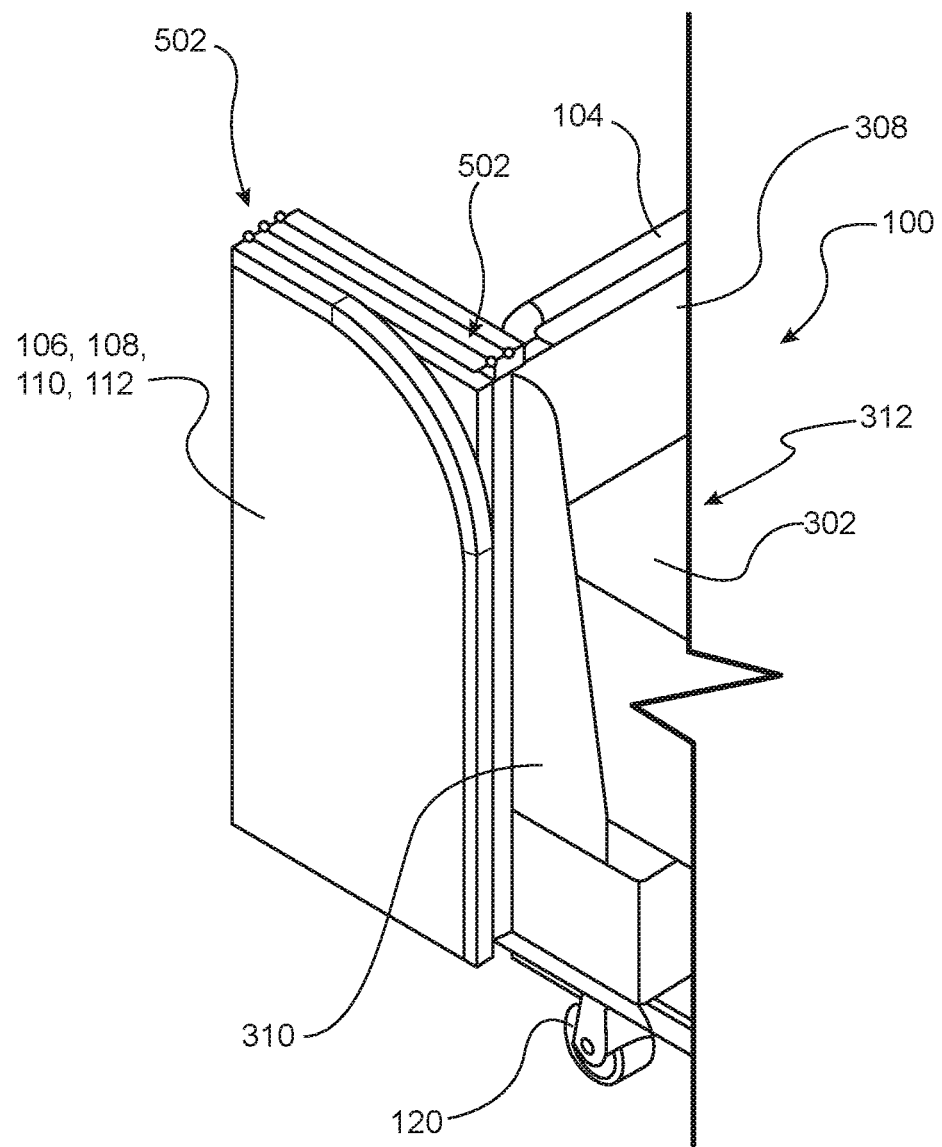
FIG. 5 shows a partial perspective view of the medical imaging supply transport cart of FIG. 1 with doors and top in an open configuration.

FIG. 5 shows a partial perspective view of the medical imaging supply transport cart of FIG. 1 with the doors open. In particular, FIG. 5 shows details of the one or more side doors 106, 108, 110, 112. Each of the one or more side doors 106, 108, 110, 112 may include a hinge structure 502 that is configured to connect one of the one or more side doors 106, 108, 110, 112 to another one of one or more side doors 106, 108, 110, 112. Additionally, one or more side doors 106, 108, 110, 112 may include a hinge structure 502 which is configured to connect to the rear wall 308. Accordingly, the hinge structures 502 are configured to allow the one or more side doors 106, 108, 110, 112 to fold in an accordion manner as illustrated in FIG. 5 to allow a user to gain full access to the medical imaging supplies 402. Other structures are contemplated as well to move the one or more side doors 106, 108, 110, 112 to a position to allow a user to gain full access to the medical imaging supplies 402.

Figure 6:
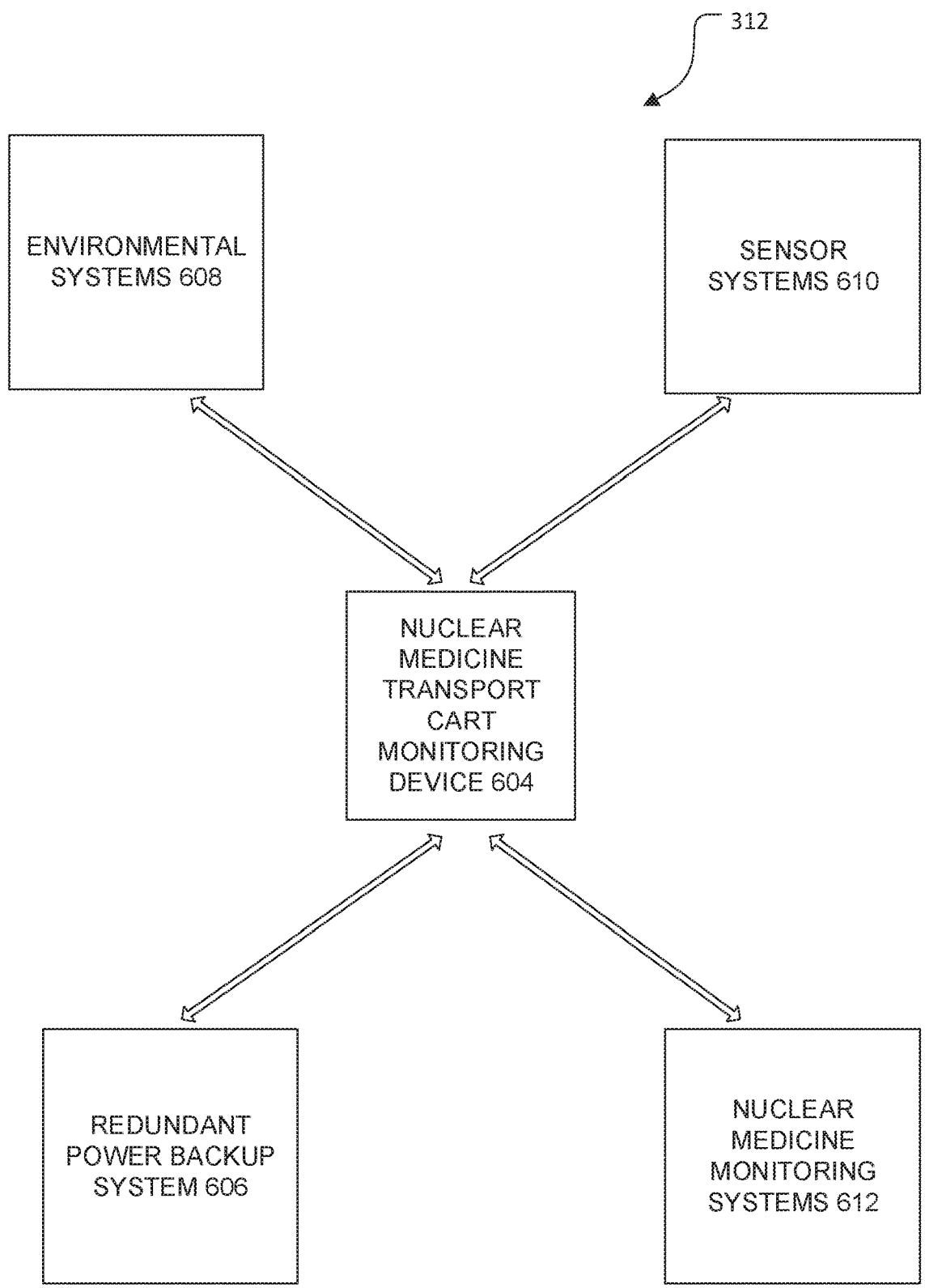
FIG. 6 shows a schematic view of a medical imaging supply transport cart monitoring and environmental control system constructed according to the principles of the disclosure.

FIG. 6 shows a schematic view of a medical imaging supply transport cart monitoring and environmental control system constructed according to the principles of the disclosure. In particular, FIG. 6 illustrates the monitoring system 312 that may include a medical imaging supply transport cart monitoring device 604, a redundant power backup system 606, environmental systems 608, sensor systems 610, a nuclear medicine monitoring system 612, and the like.

The redundant power backup system 606 may be implemented as an uninterruptible power supply or uninterruptible power source. The redundant power backup system 606 may be implemented as an electrical apparatus that provides power to the various systems of the medical imaging supply transport cart 100 when the input power source or mains power is disconnected or fails. In one aspect, the redundant power backup system 606 may use a double conversion method of accepting AC input, rectifying to DC for passing through a rechargeable battery, then inverting back to 120 V/230 V AC for powering the various systems of the medical imaging supply transport cart 100. In this regard, the medical imaging supply transport cart 100 may include a standard plug for accepting mains AC input. The batteries may be lead acid batteries, nickel cadmium batteries, lithium batteries, and the like. Additionally, various systems of the medical imaging supply transport cart 100 may also be configured to operate on DC power, in which case inverting back to 120 V/230 V AC may not be needed.

The environmental systems 608 may include systems for maintaining temperature with a heating system and/or cooling system; the environmental systems 608 may include systems for maintaining a particular humidity level with a humidifier system and/or dehumidifier system; and the environmental systems 608 may include systems purifying the air ensuring air-quality. In further aspects, the environmental systems 608 may include lighting systems. The lighting systems may be powered through the independent power backup system 606 and may include external lighting systems that light the surroundings (pathway lights), safety lights, and the like for the medical imaging supply transport cart 100 and may include internal lighting systems for lighting areas within the medical imaging supply transport cart 100. The medical imaging supply transport cart 100 may further include reflectors or reflective surfaces for easy identification in lower light conditions.

The heating system may include a heating unit such as a resistive heating unit, or the like configured to heat the air within the medical imaging supply transport cart 100. The heating system may be operated by the redundant power backup system 606 or from the mains AC input. The heating system may be controlled based on a sensed temperature from the sensor systems 610. The cooling system may include a cooling unit such as an evaporative cooling unit, mechanical cooling unit, electromechanical cooling unit, refrigerants based air conditioner, or the like configured to cool the air within the medical imaging supply transport cart 100. The cooling system may be operated by the redundant power backup system 606 or from the mains AC input. The cooling system may be controlled based on a sensed temperature from the sensor systems 610. The humidifier may be configured to add moisture to the environment of the medical imaging supply transport cart 100 and may be implemented as an evaporative humidifier, natural humidifier vaporizer, impeller humidifier, ultrasonic humidifier, or the like. The dehumidifier may be configured to extract moisture from the environment of the medical imaging supply transport cart 100 and may be implemented as part of the cooling system to extract water from the medical imaging supply transport cart 100. The air purification system may include thermodynamic sterilization, ultraviolet germicidal irradiation, filter-based purification, High-Efficiency Particulate Arrestance (HEPA) filters, polarized-media electronic air cleaners, photocatalytic oxidation (PCO) devices, photoelectrochemical oxidation devices, immobilized cell technology devices, ozone generators, titanium dioxide technology devices, and the like.

The sensor systems 610 may include a number of environmental sensors arranged throughout the medical imaging supply transport cart 100. The environmental sensors may include one or more of a temperature sensor, vibration sensor, humidity sensor, position sensors, voltage sensors, current sensors, and the like.

The temperature sensor may include one or more of a thermistor, thermocouple, resistance thermometer, silicon bandgap temperature sensor, and the like. The temperature sensor may be arranged within the medical imaging supply transport cart 100 to sense a temperature therein and control the environmental systems 608 to maintain the temperature within a desired range. The temperature sensor may also sense temperature of one or more aspects the redundant power backup system 606.

The humidity sensor may include one or more of psychrometer, hygrometer, humidistat or the like. The humidity sensor may be arranged within the medical imaging supply transport cart 100 to sense a humidity therein and control the environmental systems 608 to maintain the humidity within a desired range.

The vibration sensor may include one or more of an accelerometer or the like. The vibration sensor may be arranged within the medical imaging supply transport cart 100 to sense a vibration therein and ensure vibration is maintained below a desired value. In one aspect, the vibration sensor may be implemented as a shock data logger or vibration data logger that is configured to autonomously record shocks or vibrations over a defined period of time. Digital data is usually in the form of acceleration and time. The shock and vibration data can be retrieved (or transmitted), viewed and evaluated after it has been recorded. In one aspect, the shock and vibration data can be stored in the medical imaging supply transport cart monitoring device 604.

The position sensor may include one or more of a capacitive transducer, capacitive displacement sensor, eddy-current sensor, ultrasonic sensor, grating sensor, hall effect sensor, inductive non-contact position sensors, linear variable differential transformer, multi-axis displacement transducer, photodiode array, potentiometer, proximity sensor (optical), rotary encoder (angular), and the like. The position sensor may be arranged within the medical imaging supply transport cart 100 to sense a position of the one or more side doors 106, 108, 110, 112, the position of the top door 102, a locked state of the doors, a placement (or lack of placement) of the medical imaging supplies 402, and the like.

The voltage and current sensor may be arranged within the medical imaging supply transport cart 100 or the redundant power backup system 606 to sense a current or voltage of any aspect of the same including a battery voltage of the redundant power backup system 606.

In some aspects, the sensor systems 610 may include security system features such as a security alarm sensing tampering, lock status, and the like with the medical imaging supply transport cart 100.

The nuclear medicine monitoring systems 612 may monitor various aspects of the medical imaging supplies 402. In particular, the nuclear medicine monitoring systems 612 may monitor the number of doses provided by the medical imaging supplies 402, may monitor the amount of each of the doses provided by the medical imaging supplies 402, and the like. This monitoring may be in conjunction with the sensor systems 610 and may be implemented by one of the position sensors noted above. Alternatively, the monitoring may be in conjunction with flow sensors, volumetric sensors, or the like. Any information generated by the redundant power backup system 606, the environmental systems 608, the sensor systems 610, the nuclear medicine monitoring systems 612, and/or the like may be provided to the medical imaging supply transport cart monitoring device 604.

Figure 7:
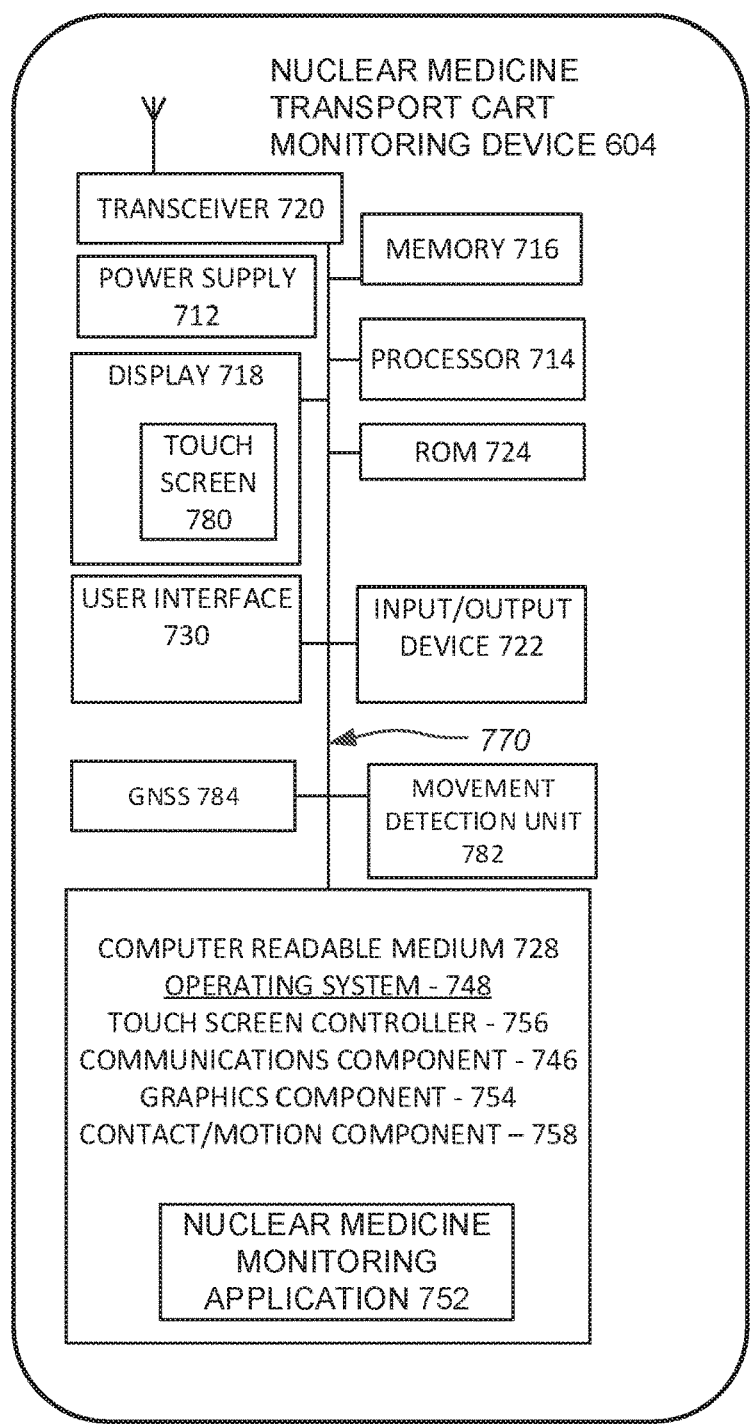
FIG. 7 shows a schematic view of a medical imaging supply transport cart monitoring device constructed according to the principles of the disclosure.

FIG. 7 shows a schematic view of a medical imaging supply transport cart monitoring device constructed according to the principles of the disclosure. The medical imaging supply transport cart monitoring device 604 may include a processor 714, a memory 716, a display 718, a user interface 730, and the like. The processor 714 may be a central processing unit, microprocessor, dedicated hardware, or the like configured to execute instructions including instructions related to software programs. The display 718 may be a liquid crystal display having a backlight to illuminate the various color liquid crystals to provide a colorful display. The user interface 730 may be any type of physical input having one or more buttons, switches, and the like and/or may be implemented as a touchscreen 780. In one aspect, the medical imaging supply transport cart monitoring device 604 may be implemented with a tablet computer, wireless phone or the like configured to provide the additional functionality as defined herein.

The medical imaging supply transport cart monitoring device 604 may further include in the memory 716 or separate from the memory 716, a computer readable medium 728, an operating system 748, a communication component 746, a contact/motion component 758, a touchscreen controller 756, a graphics component 754 and the like. The operating system 748 together with the various components providing software functionality for each of the components of the medical imaging supply transport cart monitoring device 604. The medical imaging supply transport cart monitoring device 604 may further include a read-only memory 724 (ROM) and a power supply 712 such as a battery.

The memory 716 may include a high-speed random-access memory. Also, the memory 716 may be a non-volatile memory, such as magnetic fixed disk storage, flash memory or the like. The various components of the medical imaging supply transport cart monitoring device 604 may be connected through various communication lines including a data bus 770.

Additionally, the medical imaging supply transport cart monitoring device 604 may include an input/output device 722. The input/output device 722 may be configured to receive sensor inputs from the sensor systems 610. The input/output device 722 may be configured to provide outputs to control or drive the environmental systems 608. The input/output device 722 may include an analog to digital converter and a digital to analog converter for input and output functions respectively. In some aspects, the input/ output device 722 may include USB connection, Ethernet connections, and other types of connections.

In some aspects, the input/output device 722 may include barcode reading for asset management. In this regard, the medical imaging supply transport cart monitoring device 604 may be configured to read product barcodes, location barcodes, and the like.

The medical imaging supply transport cart monitoring device 604 may include a transceiver 720 and the like. The medical imaging supply transport cart monitoring device 604 may provide radio and signal processing as needed to access a network for services over a communication channel as defined herein. The processor 714 and the transceiver 720 may be configured to process data transfer, and the like and provide other services to the medical imaging supply transport cart 100.

The touchscreen 780 of the disclosure may be implemented in the display 718 and may detect a presence and location of a touch of a user within the display area. For example, touching the display 718 of the medical imaging supply transport cart monitoring device 604 with a finger or hand. The touchscreen 780 may also sense other passive objects, such as a stylus.

In operation, the display 718 may display various objects associated with applications for execution by the processor 714. In this regard, a user may touch the display 718, and in particular the touchscreen 780, to interact with the objects. For example touching an object may execute an application in the processor 714 associated with the object that is stored in memory 716. Additionally or alternatively, touching an object may open a menu of options to be selected by the user. The display 718 may include a plurality of the objects for the user to interact with. Moreover the display 718 may include a plurality of screens. The display 718 showing one screen at a time. The user may interact with the display 718 to move a screen into view on the display 718. Various objects may be located in the each of the screens.

The touchscreen 780 may be implemented as a resistive touchscreen, a surface acoustic wave touch screen, a capacitive touch screen, a surface capacitance touchscreen, projected capacitive touch screen, self-capacitance sensors, infrared sensors, dispersive signal technology, acoustic pulse recognition, or the like.

The medical imaging supply transport cart monitoring device 604 may include a movement detection unit 782. The movement detection unit 782 may include a number of sensors to detect a movement of the medical imaging supply transport cart 100. In particular, the movement detection unit 782 may detect a movement indicating falling, sudden impact, and the like. The movement detection unit 782 may be implemented by any one or more of accelerometers, gyroscopes, altitude sensors, and/or the like. The movement detection unit 782 may further include analog-to-digital converters, filters, and the like to process the signals associated with any of the sensors.

The computer readable medium 728 may be configured to store the nuclear medicine monitoring application 752. For the purposes of this disclosure, the computer readable medium 728 stores computer data, which may include computer program code that may be executable by the processor 714 of the medical imaging supply transport cart monitoring device 604 in machine readable form. By way of example, and not limitation, the computer readable medium 728 may include computer readable storage media, for example tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules, or other data. In one or more aspects, the actions and/or events of a method, algorithm, or module may reside as one or any combination or set of codes and/or instructions on a computer readable medium 728 or machine readable medium, which may be incorporated into a computer program product.

According to another aspect of the disclosure, the medical imaging supply transport cart monitoring device 604 may estimate the location of the medical imaging supply transport cart monitoring device 604 based, at least in part, on a global navigation satellite system (GNSS 784). In another aspect, a network 802 may implement location determination based on a specific cell in which the medical imaging supply transport cart monitoring device 604 connects. In yet another aspect, a network 802 may obtain location determination based on triangulation with respect to a plurality of cells in which the medical imaging supply transport cart monitoring device 604 receives signals.

Figure 8:
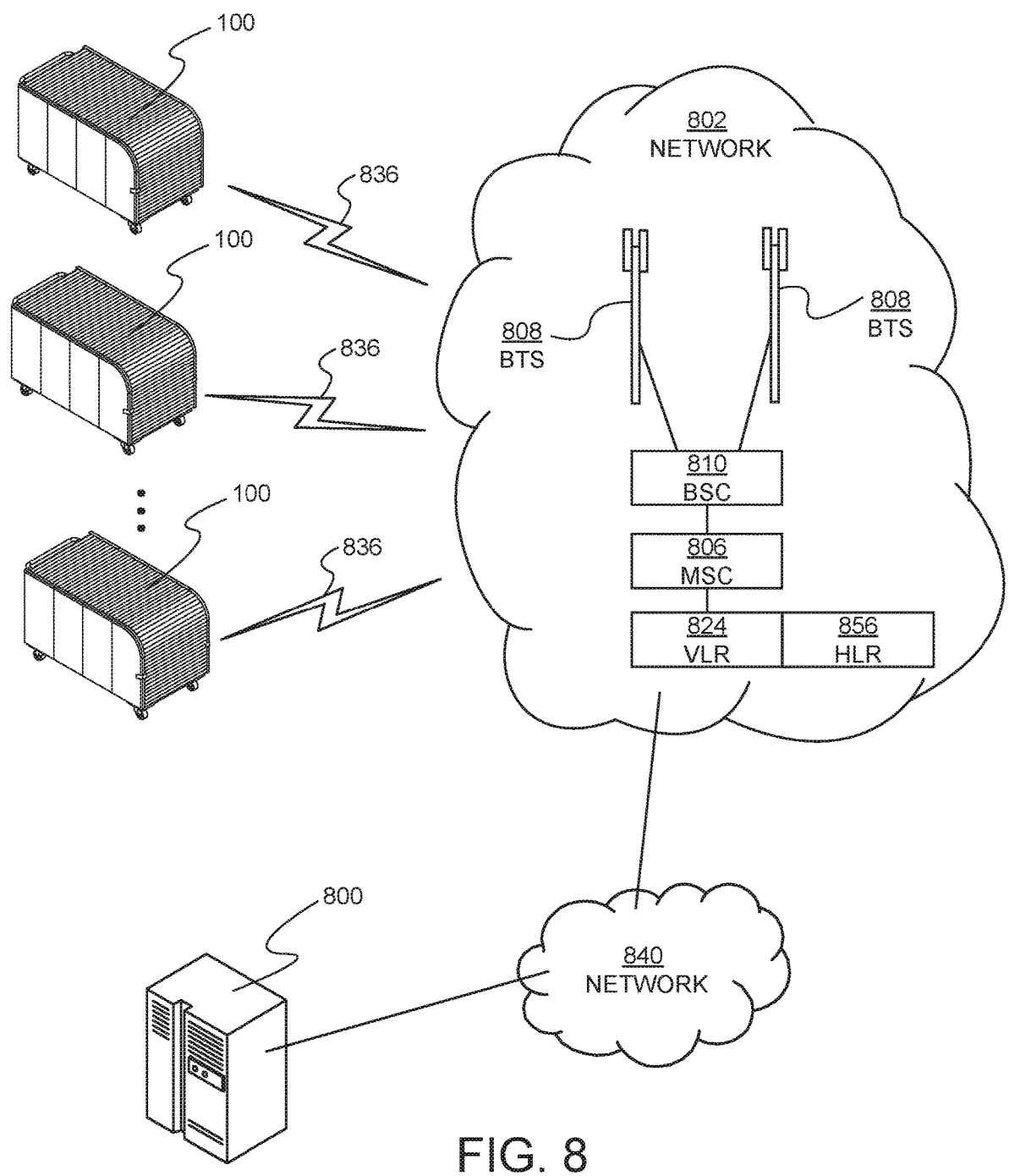
FIG. 8 shows a schematic view of a medical imaging supply transport cart monitoring system constructed according to the principles of the disclosure.

FIG. 8 shows a schematic view of a medical imaging supply transport cart monitoring system constructed according to the principles of the disclosure. The network 802 may include a base transceiver station 808 (BTS), a base station controller 810 (BSC), and a mobile switching center 806 (MSC) overseen by the network 802. Other types of wireless networks utilizing a communication channel as defined herein are contemplated as well. The mobile switching center 806 may include a Visitor Location Register (VLR 824). The base transceiver station 808 houses the radio transceivers that define a cell and handle the radio-link protocols with the medical imaging supply transport cart monitoring device 604. The base station controller manages the radio resources for one or more base transceiver stations. The base station controller 810 is the connection between the medical imaging supply transport cart monitoring device 604 and the Mobile Switching Center 806 (MSC).

A Home Location Register (HLR 856) contains all the administrative information of each medical imaging supply transport cart monitoring device 604 in the corresponding network 802, along with the current location of the medical imaging supply transport cart monitoring device 604. The above is an exemplary implementation of the network 802. Other types of networks utilizing other types of protocols may be implemented as well and are contemplated by the disclosure.

The network 802 may communicate with the medical imaging supply transport cart monitoring device 604 over a communication channel 836 as defined herein. The network 802 may further communicate over the Internet 840 to the medical imaging supply transport cart monitoring system 800. The medical imaging supply transport cart monitoring system 800 may further communicate over the Internet 840 and/or the network 802 to the medical imaging supply transport cart monitoring device 604. The use of the network 802 may be beneficial to the user as there are few geographical limitations.

In some aspects, the medical imaging supply transport cart monitoring device 604 may include artificial intelligence providing enhanced safety and control of the various mechanisms associated with the medical imaging supply transport cart 100. For example, artificial intelligence for the various sensor systems 610 readings, actuation mechanisms for lifting the cover 1002 (described below), moving the floor 304, and the like.

In some aspects, the medical imaging supply transport cart monitoring device 604 may be implemented as a personal computer (PC). The PC-based aspect having Wi-Fi capability and a hard drive storage system that implements an integrated barcode based asset management system.

Figure 9:
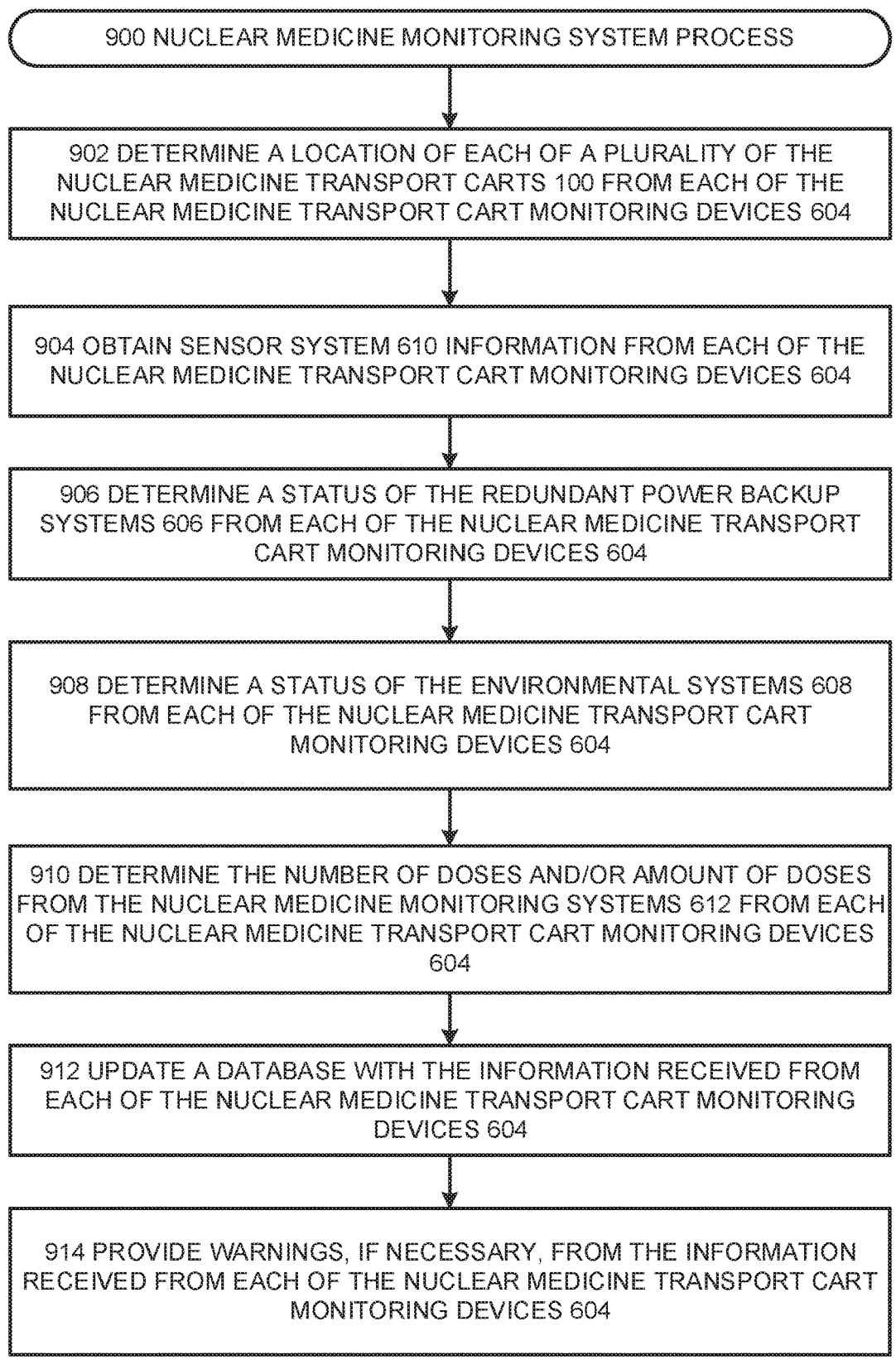
FIG. 9 illustrates a process associated with the medical imaging supply transport cart monitoring system of FIG. 8.

FIG. 9 illustrates a process associated with the medical imaging supply transport cart monitoring system of FIG. 8. In particular, FIG. 9 illustrates a nuclear medicine monitoring system process 900. The nuclear medicine monitoring system process 900 may be implemented in part by the medical imaging supply transport cart monitoring device 604 in conjunction with the nuclear medicine monitoring application 752. Alternatively or additionally, the nuclear medicine monitoring system process 900 may be implemented in part by medical imaging supply transport cart monitoring system 800. In particular, the nuclear medicine monitoring system process 900 may be configured to monitor a plurality of medical imaging supply transport carts 100.

In box 902, the nuclear medicine monitoring system process 900 may determine a location of each of a plurality of the medical imaging supply transport carts 100 from each of the medical imaging supply transport cart monitoring devices 604. In this regard, the process 900 may receive location determination information from the medical imaging supply transport cart monitoring devices 604. This location information may be determined from a global navigation satellite system (GNSS 784) implemented in the medical imaging supply transport cart monitoring devices 604. This location information is transmitted over a communication channel 836 to the medical imaging supply transport cart monitoring system 800. The medical imaging supply transport cart monitoring system 800 may store the location information in an associated database.

In box 904 the nuclear medicine monitoring system process 900 may obtain sensor systems 610 information from each of the medical imaging supply transport cart monitoring devices 604. This sensor information may be transmitted over a communication channel 836 to the medical imaging supply transport cart monitoring system 800. The medical imaging supply transport cart monitoring system 800 may store the sensor information in the database.

In box 906 the nuclear medicine monitoring system process 900 may determine a status of the redundant power backup system 606 from each of the medical imaging supply transport cart monitoring devices 604. This status information may be transmitted over a communication channel 836 to the medical imaging supply transport cart monitoring system 800. The medical imaging supply transport cart monitoring system 800 may store the status information in the database.

In box 908 the nuclear medicine monitoring system process 900 may determine a status of the environmental systems 608 from each of the medical imaging supply transport cart monitoring devices 604. This status information may be transmitted over a communication channel 836 to the medical imaging supply transport cart monitoring system 800. The medical imaging supply transport cart monitoring system 800 may store the status information in the database.

In box 910 the nuclear medicine monitoring system process 900 may determine the number of doses and/or amount of doses from the nuclear medicine monitoring systems 612 from each of the medical imaging supply transport cart monitoring devices 604. This dose information may be transmitted over a communication channel 836 to the medical imaging supply transport cart monitoring system 800. The medical imaging supply transport cart monitoring system 800 may store the dose information in the database. In one aspect the dose information stored in the database may be utilized for subsequent billing to medical facilities and/or physicians. In a further aspect, the dose information may be utilized to determine when the medical imaging supplies 402 needs to be restocked with doses.

In box 912 the nuclear medicine monitoring system process 900 may update a database with the information received from each of the medical imaging supply transport cart monitoring devices 604. The information may be the information noted above or additional information. This updated information may be transmitted over a communication channel 836 to the medical imaging supply transport cart monitoring system 800. The medical imaging supply transport cart monitoring system 800 may store the updated information in the database.

In a particular aspect, the medical imaging supply transport cart monitoring system 800 may function as an asset management system providing tracking of the medical imaging supply transport carts 100.

In box 914 the nuclear medicine monitoring system process 900 may provide warnings, if necessary, from the information received from each of the medical imaging supply transport cart monitoring devices 604. In this regard, the nuclear medicine monitoring system process 900 may compare the information received to desired or expected values. If the information is within a range of desired or expected values, then no action is taken. On the other hand, if the information is outside a range of desired or expected values, then the nuclear medicine monitoring system process 900 may provide warnings via a web interface, email transmission, text message transmission, or the like for a user to take appropriate action.

Figure 10:
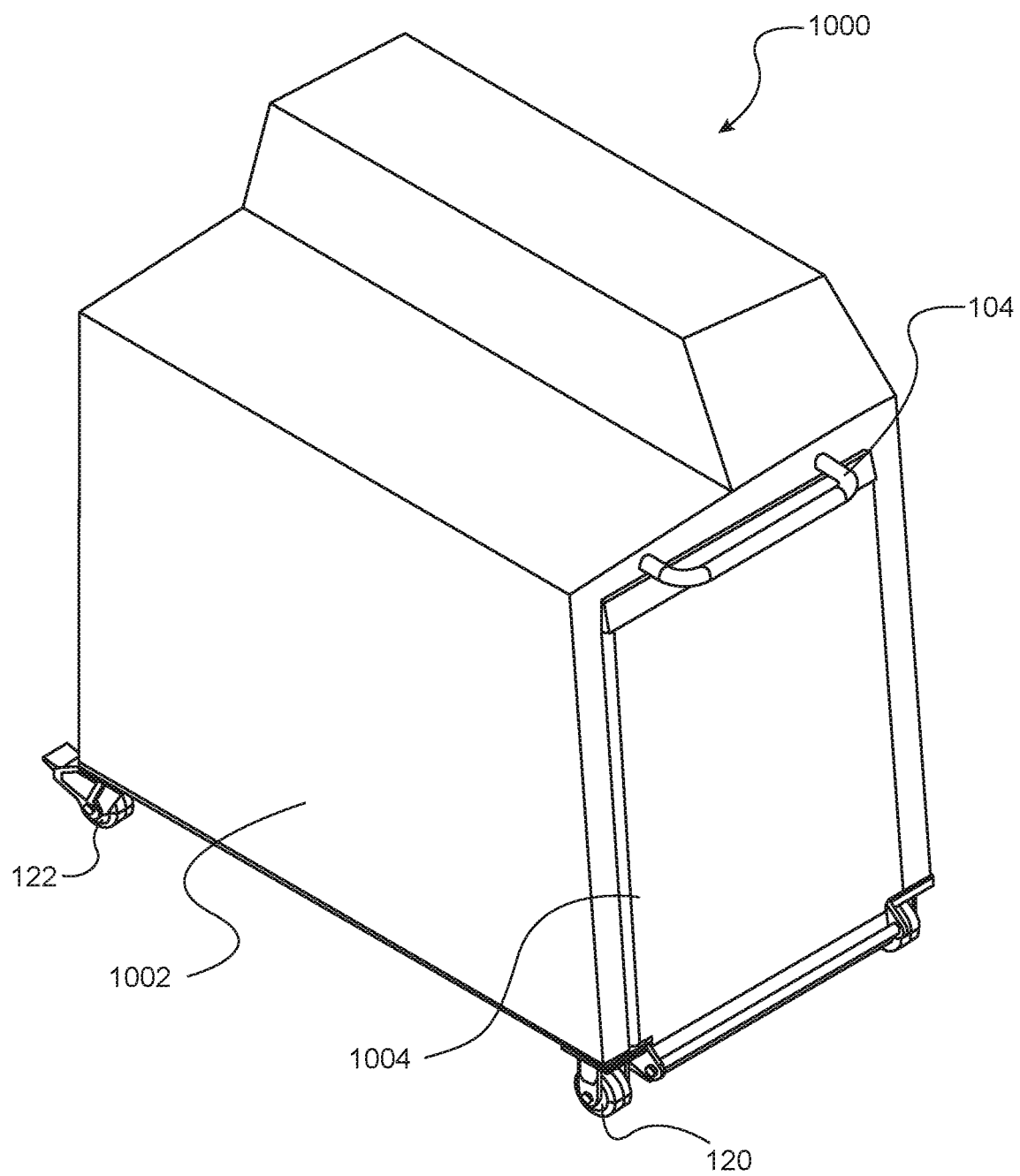
FIG. 10 shows a perspective view of another aspect of a medical imaging supply transport cart with doors and top in a closed configuration constructed according to the principles of the disclosure.
Figure 11:
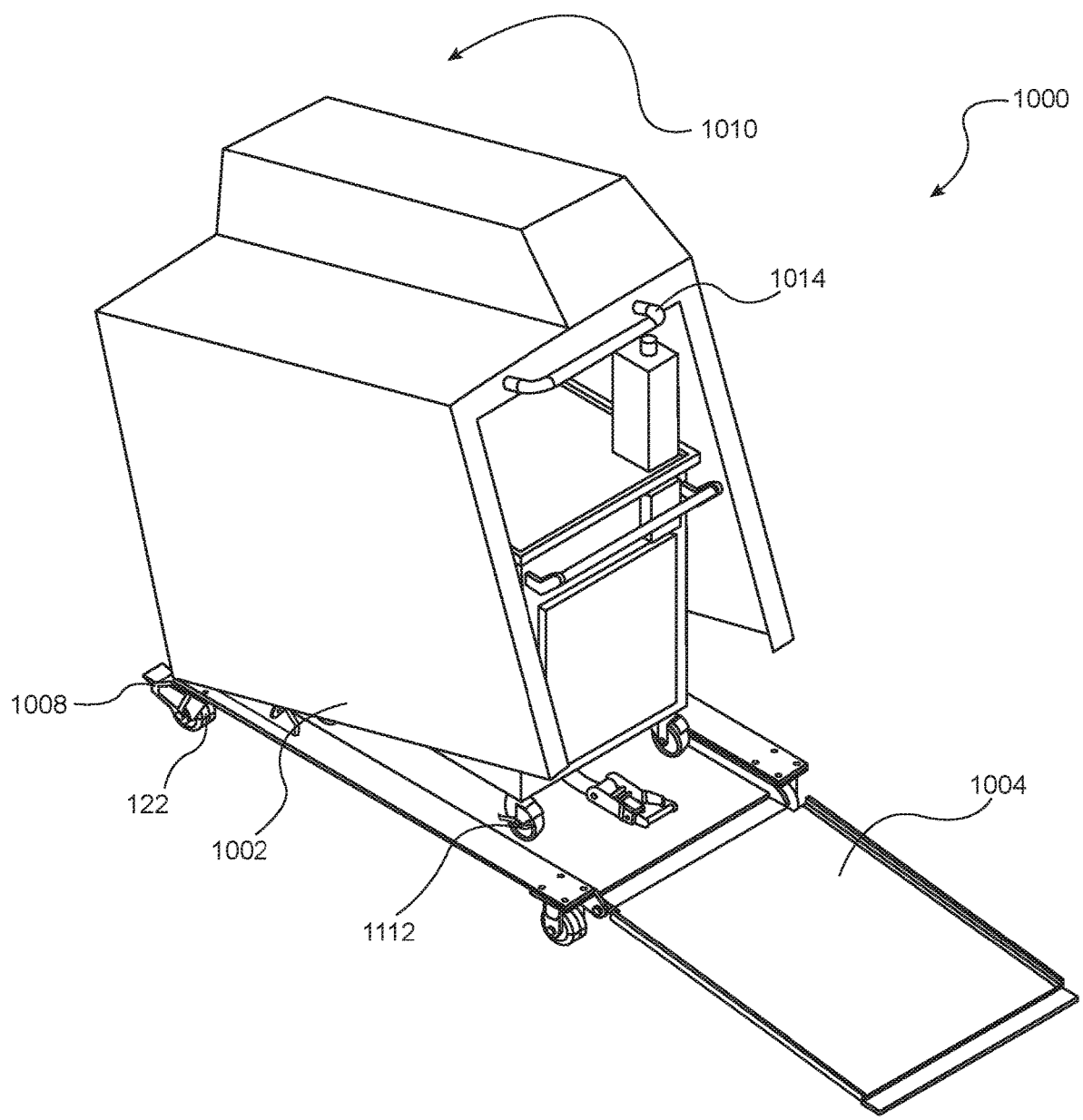
FIG. 11 shows a perspective view of the medical imaging supply transport cart of FIG. 10 with the door open and the top partially open.
Figure 12:
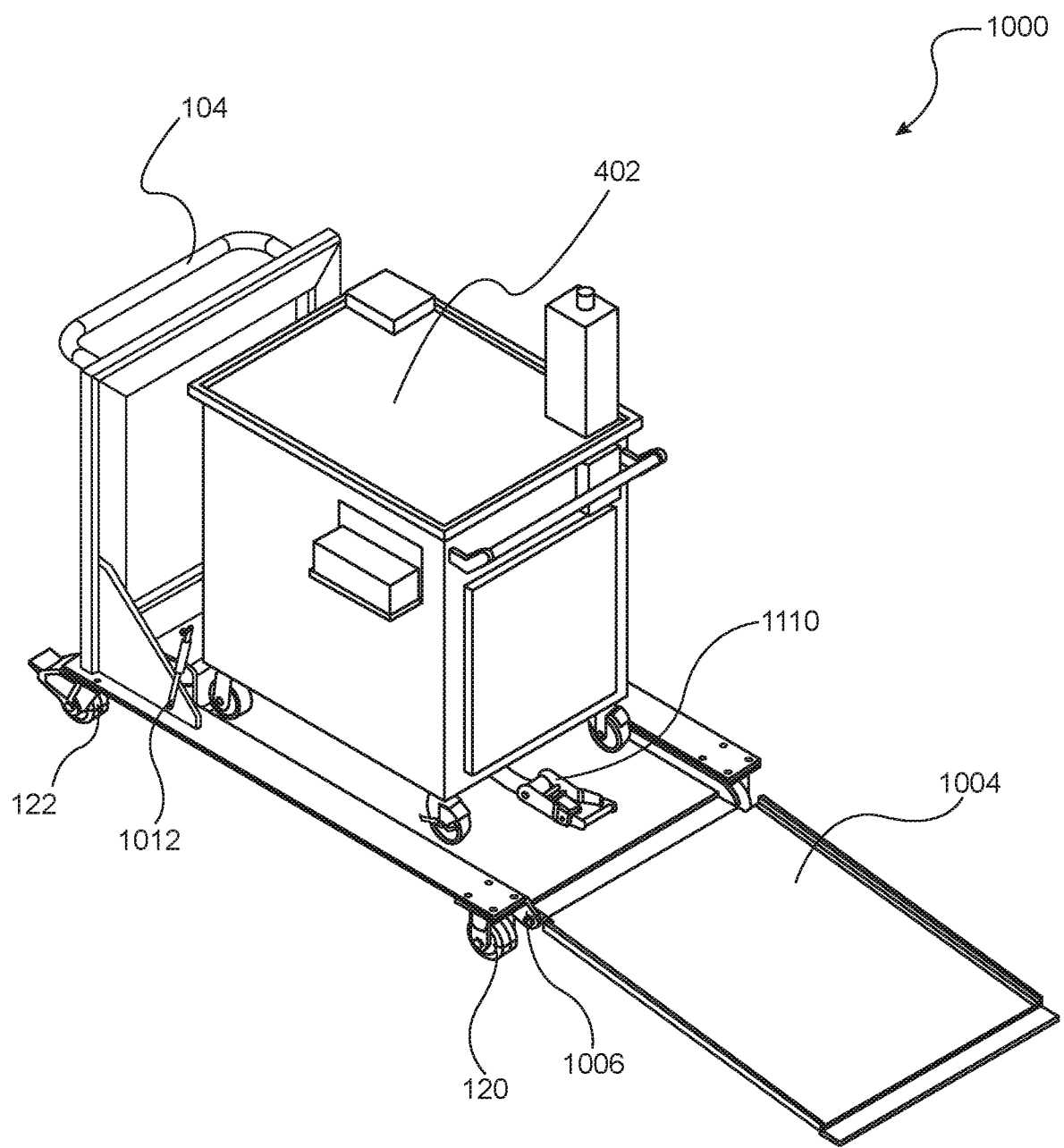
FIG. 12 shows a perspective view of the medical imaging supply transport cart of FIG. 10 with door in an open configuration and the top removed.

FIG. 10 shows a perspective view of another aspect of a medical imaging supply transport cart with doors and top in a closed configuration constructed according to the principles of the disclosure; FIG. 11 shows a perspective view of the medical imaging supply transport cart of FIG. 10 with the door open and the top partially open; and FIG. 12 shows a perspective view of the medical imaging supply transport cart of FIG. 10 with door in an open configuration and the top removed. In particular, FIGS. 10-12 show another aspect of a medical imaging supply transport cart 1000 that may include any one or more of the same features of the medical imaging supply transport cart 400.

The medical imaging supply transport cart 1000 may further include a cover 1002. The cover 1002 may include a pivot or hinge structure 1008 allowing the cover 1002 to rotate upwardly in the direction of arrow 1010 to gain access to the medical imaging supplies 402. The cover 1002 may include an actuator mechanism 1012 as shown in FIG. 12. The actuator mechanism 1012 may include a hydraulic system, pneumatic system, mechanical system, or the like that moves cover 1002 from the closed position shown in FIG. 10 to an open position. In aspects where the actuation mechanism implemented as the hydraulic system, the hydraulic system may include a source of pressurized hydraulic fluid, a hydraulic cylinder to move the cover 1002, and a controller that controls both the pressurized hydraulic fluid source and the hydraulic cylinder. In aspects where the actuation mechanism implemented as the pneumatic system, the pneumatic system may include a source of pressurized pneumatic fluid, a pneumatic cylinder to move the cover 1002, and a controller that controls both the pressurized pneumatic fluid source and the pneumatic cylinder. In aspects where the actuation mechanism implemented as the mechanical system, the mechanical system may include a source of mechanical movement such as an electric motor or by a handcrank, a mechanical device such as a rack and pinion, gears, chains, and the like to move the cover 1002, and a controller that controls both.

The medical imaging supply transport cart 1000 may further include a ramp 1004. The ramp 1004 may also have a dual purpose of acting as a door as shown in FIG. 10. The ramp 1004 may be moved to a position as shown in FIG. 12 to allow the medical imaging supplies 402, if implemented with wheels 1112, to be easily rolled out of the medical imaging supply transport cart 1000 for use. In this regard, the ramp 1004 may include a hinge structure 1006 so that the ramp 1004 may be easily moved between open and closed positions. In one aspect, the medical imaging supply transport cart 1000 may include a second handle 1014.

Accordingly, the disclosure has set forth a medical imaging supply transport cart having enhanced safety features and a process implementing the same to reduce the complexity and costs associated with using nuclear medicine dose supply devices and/or the medical imaging supplies 402. The medical imaging supply transport cart as described herein is designed to be easily transported to medical facilities and provide the needed doses of nuclear medicine with higher levels of safety and greater ease of transportation resulting in more secure radioactive material management, lower diagnostic medical costs and better patient care. Moreover, the medical imaging supply transport cart as described herein is configured to be safely transported in a small delivery truck.

In one aspect, a small delivery truck is a truck that is smaller than a tractor-trailer. In one aspect, a small delivery truck is a truck that is less than 60 feet in length. In one aspect, a small delivery truck is a truck that is less than 30 feet in length. In one aspect, a small delivery truck is a truck that is less than 25 feet in length. In one aspect, a small delivery truck is a truck that is not associated with a continuous climate controlled environment (cooled and heated only when the engine is operating). In one aspect, the small delivery truck may include platform lift technology for lifting the medical imaging supply transport carts 100, 1000 into and out of the small delivery truck. In one aspect, the small delivery truck may include integrated retractable arms or hoisting mechanisms for lifting the medical imaging supply transport carts 100, 1000 into and out of the small delivery truck. Such mechanisms may be mounted inside of the small delivery truck so as to not protrude from the side or rear. The small delivery truck may further include an identification device consistent with one or more of the features the medical imaging supply transport cart monitoring device 604 described in detail above.

In one aspect, the medical imaging supplies 402 may be an infusion system configured to store and provide dose quantities of radionuclides to the patient for use with the PET system that includes rubidium-82. The medical imaging supplies 402 may include an identification device. The identification device may be Bluetooth or Wireless Fidelity enabled. For example, the identification device may be a Zebra Mpact beacon that may be obtained from ZIH Corporation. The medical imaging supply transport carts 100, 1000 may transport this particular kind of medical imaging supplies 402. The medical imaging supply transport carts 100, 1000 may include the features noted above and the medical imaging supply transport cart monitoring devices 604 may be implemented with a Bosch XDK sensor kit integrated with a Zebra Zatar IoT (Internet of things) platform. Additionally, the medical imaging supply transport cart monitoring devices 604 may include a TC75 WAN and GNSS enabled device operating an android system that may be obtained from ZIH Corporation. In one aspect, the medical imaging supply transport cart monitoring devices 604 may include a cradle or mount for the TC75 implementation of the medical imaging supply transport cart monitoring devices 604. The medical imaging supply transport cart monitoring devices 604 may communicate with a central repository/hosted application for data collection, real time information, historical data, view routes between sites, tracking, schedule managing, auto detection of driver interaction, and the like as described with respect to FIGS. 8 and 9. Moreover, the small delivery truck may also include an identification device. For example, the identification device may be a Zebra Mpact beacon that may be obtained from ZIH Corporation noted above.

In another aspect, the medical imaging supplies 402 may be a rubidium-82 generator to store dose quantities of radionuclides to the patient for use with the PET system. The medical imaging supplies 402 may include an identification device. The identification device may be Bluetooth or Wireless Fidelity enabled. For example, the identification device may be a Zebra Mpact beacon that may be obtained from ZIH Corporation. The medical imaging supply transport carts 100, 1000 may transport this particular kind of medical imaging supplies 402. The medical imaging supply transport carts 100, 1000 may include the features noted above and the medical imaging supply transport cart monitoring devices 604 may be implemented with a Bosch XDK sensor kit integrated with a Zebra Zatar IoT (Internet of things) platform. Additionally, the medical imaging supply transport cart monitoring devices 604 may include a TC75 WAN and GNSS enabled device operating an android system that may be obtained from ZIH Corporation. In one aspect, the medical imaging supply transport cart monitoring devices 604 may include a cradle or mount for the TC75 implementation of the medical imaging supply transport cart monitoring devices 604. The medical imaging supply transport cart monitoring devices 604 may communicate with a central repository/hosted application for data collection, real time information, historical data, view routes between sites, tracking, schedule managing, auto detection of driver interaction, and the like as described with respect to FIGS. 8 and 9. Moreover, the small delivery truck may also include an identification device. For example, the identification device may be a Zebra Mpact beacon that may be obtained from ZIH Corporation noted above.

In one aspect, the medical imaging supplies 402 may be molecular isotopes, such as Fluorine 18, that may be packaged in lead encased containers which have a minimum of 1 inch lead shielding and weigh between 21 to 40 pounds each. The medical imaging supplies 402 may include an identification device. The identification device may be Bluetooth or Wireless Fidelity enabled. For example, the identification device may be a Zebra Mpact beacon that may be obtained from ZIH Corporation. The medical imaging supply transport carts 100, 1000 may transport this particular kind of medical imaging supplies 402. The medical imaging supply transport carts 100, 1000 may include the features noted above and the medical imaging supply transport cart monitoring devices 604 may be implemented with a Bosch XDK sensor kit integrated with a Zebra Zatar IoT (Internet of things) platform. Additionally, the medical imaging supply transport cart monitoring devices 604 may include a TC75 WAN and GNSS enabled device operating an android system that may be obtained from ZIH Corporation. In one aspect, the medical imaging supply transport cart monitoring devices 604 may include a cradle or mount for the TC75 implementation of the medical imaging supply transport cart monitoring devices 604. The medical imaging supply transport cart monitoring devices 604 may communicate with a central repository/hosted application for data collection, real time information, historical data, view routes between sites, tracking, schedule managing, auto detection of driver interaction, and the like as described with respect to FIGS. 8 and 9. Moreover, the small delivery truck may also include an identification device. For example, the identification device may be a Zebra Mpact beacon that may be obtained from ZIH Corporation noted above.

Aspects of the disclosure may include communication channels that may be any type of wired or wireless electronic communications network, such as, e.g., a wired/wireless local area network (LAN), a wired/wireless personal area network (PAN), a wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, Near field communication (NFC), a cellular telephone network, a Personal Communications Service (PCS), using known protocols such as the Global System for Mobile Communications (GSM), CDMA (Code-Division Multiple Access), GSM/EDGE and UMTS/HSPA network technologies, Long Term Evolution (LTE), 5G (5th generation mobile networks or 5th generation wireless systems), WiMAX, HSPA+, W-CDMA (Wideband Code-Division Multiple Access), CDMA2000 (also known as C2K or IMT Multi-Carrier (IMT-MC)), Wireless Fidelity (Wi-Fi), Bluetooth, and/or the like, and/or a combination of two or more thereof. The NFC standards cover communications protocols and data exchange formats, and are based on existing radio-frequency identification (RFID) standards including ISO/IEC 14443 and FeliCa. The standards include ISO/IEC 78092[3] and those defined by the NFC Forum.

Aspects of the disclosure may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

Aspects of the disclosure may be web-based. For example, a server may operate a web application in conjunction with a database. The web application may be hosted in a browser-controlled environment (e.g., a Java applet and/or the like), coded in a browser-supported language (e.g., JavaScript combined with a browser-rendered markup language (e.g., Hyper Text Markup Language (HTML) and/or the like)) and/or the like such that any computer running a common web browser (e.g., Internet Explorer™, Firefox™, Chrome™, Safari™ or the like) may render the application executable. A web-based service may be more beneficial due to the ubiquity of web browsers and the convenience of using a web browser as a client (i.e., thin client). Further, with inherent support for cross-platform compatibility, the web application may be maintained and updated without distributing and installing software on each.

Aspects of the disclosure may be implemented in any type of mobile smartphones that are operated by any type of advanced mobile data processing and communication operating system, such as, e.g., an Apple™ iOS™ operating system, a Google™ Android™ operating system, a RIM™ Blackberry™ operating system, a Nokia™ Symbian™ operating system, a Microsoft™ Windows Mobile™ operating system, a Microsoft™ Windows Phone™ operating system, a Linux™ operating system or the like.

Further in accordance with various aspects of the disclosure, the methods described herein are intended for operation with dedicated hardware implementations including, but not limited to, PCs, PDAs, semiconductors, application specific integrated circuits (ASIC), programmable logic arrays, cloud computing devices, and other hardware devices constructed to implement the methods described herein.

It should also be noted that the software implementations of the disclosure as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the disclosure is considered to include a tangible storage medium or distribution medium, as listed herein and including art-recognized equivalents and successor media, in which the software implementations herein are stored.

Additionally, the various aspects of the disclosure may be implemented in a non-generic computer implementation. Moreover, the various aspects of the disclosure set forth herein improve the functioning of the system as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the system overall in its specific implementation to perform the process set forth by the disclosure and as defined by the claims.

According to an example, the global navigation satellite system (GNSS) may include a device and/or system that may estimate its location based, at least in part, on signals received from space vehicles (SVs). In particular, such a device and/or system may obtain "pseudorange" measurements including approximations of distances between associated SVs and a navigation satellite receiver. In a particular example, such a pseudorange may be determined at a receiver that is capable of processing signals from one or more SVs as part of a Satellite Positioning System (SPS). Such an SPS may comprise, for example, a Global Positioning System (GPS), Galileo, Glonass, to name a few, or any SPS developed in the future. To determine its location, a satellite navigation receiver may obtain pseudorange measurements to three or more satellites as well as their positions at time of transmitting. Knowing the SV orbital parameters, these positions can be calculated for any point in time. A pseudorange measurement may then be determined based, at least in part, on the time a signal travels from an SV to the receiver, multiplied by the speed of light. While techniques described herein may be provided as implementations of location determination in GPS and/or Galileo types of SPS as specific illustrations according to particular examples, it should be understood that these techniques may also apply to other types of SPS, and that claimed subject matter is not limited in this respect.

Aspects of the disclosure may include a server executing an instance of an application or software configured to accept requests from a client and giving responses accordingly. The server may run on any computer including dedicated computers. The computer may include at least one processing element, typically a central processing unit (CPU), and some form of memory. The processing element may carry out arithmetic and logic operations, and a sequencing and control unit may change the order of operations in response to stored information. The server may include peripheral devices that may allow information to be retrieved from an external source, and the result of operations saved and retrieved. The server may operate within a client-server architecture. The server may perform some tasks on behalf of clients. The clients may connect to the server through the network on a communication channel as defined herein. The server may use memory with error detection and correction, redundant disks, redundant power supplies and so on.

The many features and advantages of aspects of the disclosure are apparent from the detailed specification, and, thus, it is intended by the appended claims to cover all such features and advantages of aspects of the disclosure which fall within the true spirit and scope of aspects of the disclosure. Further, since numerous modifications and variations will readily occur to those skilled in the art, it is not desired to limit aspects of the disclosure to the exact construction and operation illustrated and described, and, accordingly, all suitable modifications and equivalents may be resorted to that fall within the scope of aspects of the disclosure.

What is claimed is:

1. A medical imaging supply transport cart system comprising:
   a supply transport cart; and
   a medical imaging infusion system;
   the supply transport cart comprising:
      a floor surface configured to support the medical imaging infusion system;
      a bottom portion configured to support the floor surface;
      a first securing mechanism configured to secure the medical imaging infusion system within the supply transport cart;
      a first plurality of wheels arranged below the floor surface;
      at least one door configured to enclose the medical imaging infusion system within the supply transport cart; and
      a handle configured to be grasped by a user to guide the supply transport cart;
   the medical imaging infusion system comprising:
      a second plurality of wheels configured to roll the medical imaging infusion system onto and off the floor surface of the supply transport cart;
      at least one dose of a nuclear medicine; and
      a nuclear medicine monitoring system, the nuclear medicine monitoring system configured to monitor at least one of the following: a number of doses of a nuclear medicine provided by the medical imaging infusion system and monitor an amount of each of the doses of the nuclear medicine provided by the medical imaging infusion system.

2. The medical imaging supply transport cart system according to claim 1
   wherein the at least one door is configured to move between an open position and a closed position;
   wherein when the at least one door is in the open position, the at least one door is configured as a ramp for the medical imaging infusion system to roll onto and off the floor surface of the supply transport cart; and wherein the supply transport cart further comprises a shock absorbing mechanism.

3. The medical imaging supply transport cart system according to claim 1 further comprising:
a second securing mechanism configured to rigidly secure the medical imaging supply transport cart within a small delivery truck during transportation.

4. The medical imaging supply transport cart system according to claim 1 wherein at least one of the first plurality of wheels is configured with a motor to propel the supply transport cart.

5. The medical imaging supply transport cart system according to claim 1 further comprising:
at least one of the following: environmental systems, sensor systems, and a redundant power backup system; and
at least one monitoring device configured to monitor at least one of the following:
the environmental systems, the sensor systems, and the redundant power backup system.

6. The medical imaging supply transport cart system according to claim 5
wherein the at least one monitoring device comprises a tablet computer; and
wherein the at least one monitoring device is configured to estimate a location of the at least one monitoring device based on a global navigation satellite system.

7. The medical imaging supply transport cart system according to claim 5 further comprising the environmental systems,
wherein the environmental systems are configured to control an environment of the supply transport cart, the environmental systems comprising a cooling unit and at least one of the following: a heating unit, a humidification unit, dehumidification unit, and an air purification unit.

8. The medical imaging supply transport cart system according to claim 5 further comprising the sensor systems,
wherein the sensor systems are configured to sense an environment of the supply transport cart, the sensor systems comprising at least a temperature sensor and a motion sensor.

9. The medical imaging supply transport cart system according to claim 5 further comprising the redundant power backup system,
wherein the redundant power backup system is configured to provide power to the supply transport cart, the redundant power backup system comprising at least one power storage device.

10. A medical imaging supply transport cart monitoring system comprising the medical imaging supply transport cart system according to claim 5, the system further comprising:
a medical imaging supply transport cart monitoring system configured to monitor a plurality of medical imaging supply transport carts; and
each of the plurality of medical imaging supply transport carts comprising the at least one monitoring device configured to connect to a wireless network and exchange information across the wireless network to the medical imaging supply transport cart monitoring system.

11. The system according to claim 10 wherein the medical imaging supply transport cart monitoring system is configured to monitor a location of the at least one monitoring device, each of the monitoring devices being associated with one of a plurality of medical imaging supply transport carts and configured to estimate a location based on a global navigation satellite system.

12. A medical imaging supply transport cart system comprising:
a supply transport cart; and
a medical imaging infusion system;
the supply transport cart comprising:
a floor surface configured to support the medical imaging infusion system;
a bottom portion configured to support the floor surface;
a first securing mechanism configured to secure the medical imaging infusion system within the supply transport cart;
a first plurality of wheels arranged below the floor surface;
at least one door configured to enclose the medical imaging infusion system within the supply transport cart;
a handle configured to be grasped by a user to guide the supply transport cart; and
sensor systems configured to sense an environment of the supply transport cart, the sensor systems comprising at least a temperature sensor and a motion sensor;
the medical imaging infusion system comprising:
a second plurality of wheels configured to roll the medical imaging infusion system onto and off the floor surface of the supply transport cart; and
at least one dose of a nuclear medicine.

13. The medical imaging supply transport cart system according to claim 12 wherein the at least one door is configured to move between an open position and a closed position;
wherein when the at least one door is in the open position, the at least one door is configured as a ramp for the medical imaging infusion system to roll onto and off the floor surface of the supply transport cart; and
wherein the supply transport cart further comprises a shock absorbing mechanism.

14. The medical imaging supply transport cart system according to claim 12 further comprising:
a second securing mechanism configured to rigidly secure the medical imaging supply transport cart within a small delivery truck during transportation.

15. The medical imaging supply transport cart system according to claim 12 further comprising:
at least one locking mechanism associated with the at least one door, the at least one locking mechanism configured to lock the at least one door in a closed position.

16. The medical imaging supply transport cart system according to claim 12 further comprising:
at least one of the following: environmental systems, sensor systems, and a redundant power backup system; and
at least one monitoring device configured to monitor at least one of the following: the environmental systems, the sensor systems, and the redundant power backup system.

17. The medical imaging supply transport cart system according to claim 16
wherein the at least one monitoring device comprises a tablet computer; and wherein the at least one monitoring device is configured to estimate a location of the at least one monitoring device based on a global navigation satellite system.

18. The medical imaging supply transport cart system according to claim 16 further comprising the environmental systems,
   wherein the environmental systems are configured to control an environment of the supply transport cart, the environmental systems comprising a cooling unit and at least one of the following: a heating unit, a humidification unit, dehumidification unit, and an air purification unit.

19. The medical imaging supply transport cart system according to claim 16 further comprising the redundant power backup system,
   wherein the redundant power backup system is configured to provide power to the supply transport cart, the redundant power backup system comprising at least one power storage device.

20. A medical imaging supply transport cart monitoring system comprising the medical imaging supply transport cart system according to claim 16, the system further comprising:
   a medical imaging supply transport cart monitoring system configured to monitor a plurality of medical imaging supply transport carts; and
   each of the plurality of medical imaging supply transport carts comprising the at least one monitoring device configured to connect to a wireless network and exchange information across the wireless network to the medical imaging supply transport cart monitoring system.

21. The system according to claim 20 wherein the medical imaging supply transport cart monitoring system is configured to monitor a location of the at least one monitoring device, each of the monitoring devices being associated with one of a plurality of medical imaging supply transport carts and configured to estimate a location based on a global navigation satellite system.

* * * * *